United States Patent
Bae et al.

(10) Patent No.: US 10,098,855 B2
(45) Date of Patent: Oct. 16, 2018

(54) COMPOSITION COMPRISING ASM INHIBITOR AS ACTIVE INGREDIENT FOR PREVENTING OR TREATING DEGENERATIVE NEUROLOGICAL DISORDERS

(71) Applicant: KYUNGPOOK NATIONAL UNIVERSITY INDUSTRY—ACADEMIC COOPERATION FOUNDATION, Daegu (KR)

(72) Inventors: Jae Sung Bae, Daegu (KR); Hee Kyung Jin, Daegu (KR); Min Hee Park, Gyeongsan-si (KR)

(73) Assignee: KYUNGPOOK NATIONAL UNIVERSITY INDUSTRY—ACADEMIC COOPERATION FOUNDATION, Daegu (KR)

( * ) Notice: Subject to any disclaimer, the term of this patent is extended or adjusted under 35 U.S.C. 154(b) by 0 days.

(21) Appl. No.: 14/889,293

(22) PCT Filed: May 7, 2014

(86) PCT No.: PCT/KR2014/004025
§ 371 (c)(1),
(2) Date: Nov. 5, 2015

(87) PCT Pub. No.: WO2014/182051
PCT Pub. Date: Nov. 13, 2014

(65) Prior Publication Data
US 2016/0101070 A1    Apr. 14, 2016

(30) Foreign Application Priority Data
May 7, 2013    (KR) ........................ 10-2013-0051279

(51) Int. Cl.
| G01N 33/53 | (2006.01) |
| G01N 33/559 | (2006.01) |
| G01N 33/561 | (2006.01) |
| G01N 33/573 | (2006.01) |
| A61K 31/137 | (2006.01) |
| C07K 16/18 | (2006.01) |
| A01K 67/027 | (2006.01) |
| C12N 15/113 | (2010.01) |
| C12Q 1/6883 | (2018.01) |
| G01N 33/50 | (2006.01) |
| G01N 33/68 | (2006.01) |
| A61K 48/00 | (2006.01) |

(52) U.S. Cl.
CPC ........ *A61K 31/137* (2013.01); *A01K 67/0275* (2013.01); *C07K 16/18* (2013.01); *C12N 15/1137* (2013.01); *C12Q 1/6883* (2013.01); *G01N 33/5023* (2013.01); *G01N 33/53* (2013.01); *G01N 33/559* (2013.01); *G01N 33/561* (2013.01); *G01N 33/573* (2013.01); *A01K 2217/15* (2013.01); *A01K 2227/105* (2013.01); *A01K 2267/0312* (2013.01); *A61K 48/005* (2013.01); *C12N 2320/30* (2013.01); *C12Q 2600/136* (2013.01); *C12Q 2600/158* (2013.01); *C12Y 301/04012* (2013.01); *G01N 33/6896* (2013.01); *G01N 2333/916* (2013.01); *G01N 2800/28* (2013.01); *G01N 2800/50* (2013.01); *G01N 2800/52* (2013.01)

(58) Field of Classification Search
CPC .. G01N 33/53; G01N 33/573; G01N 33/6896; G01N 2800/50; G01N 2800/52; G01N 2800/28
See application file for complete search history.

(56) References Cited

FOREIGN PATENT DOCUMENTS

| KR | 10-2001-0045120 A | 6/2001 |
| KR | 10-1214198 B1 | 12/2012 |

OTHER PUBLICATIONS

Benkirane et al., Exploration of requirements for peptidomimetic immune recognition. Antigenic and immunogenic properties of reduced peptide bond pseudopeptide analogues of a histone hexapeptide, J. Biol. Chem., 271(52):33218-24 (1996).
Ellington et al., In vitro selection of RNA molecules that bind specific ligands, Nature, 346(6287):818-22 (1990).
Famulok et al., Nucleic acid aptamers—from selection in vitro to applications in vivo, Acc. Chem. Res., 33(9):591-9 (2000).
International Search Report and Written Opinion, International Application No. PCT/KR2014/004025, dated Aug. 21, 2014.
(Continued)

*Primary Examiner* — Robert C Hayes
(74) *Attorney, Agent, or Firm* — Sughrue Mion, PLLC

(57) ABSTRACT

The present invention relates to a composition comprising an ASM inhibitor as an active ingredient for preventing or treating degenerative neurological diseases. According to the present invention, when ASM is partially removed in an Alzheimer's disease model mouse, that is when ASM is inhibited therein, such when as an Alzheimer's disease model mouse with a partial removal of ASM is in a parabionic union with an Alzheimer's disease model mouse, or when an Alzheimer's disease model mouse is injected with the serum of an Alzheimer's disease model mouse from which ASM gene has been removed, the deposition of β-amyloid in the brain tissue is inhibited and the ability to learn and remember are improved, and the present invention confirms such superb effects. Accordingly, ASM inhibitor can be effectively used to prevent or treat degenerative neurological diseases.

3 Claims, 37 Drawing Sheets

(56) References Cited

OTHER PUBLICATIONS

Park et al., Rationally designed anti-HER2/neu peptide mimetic disables P185HER2/neu tyrosine kinases in vitro and in vivo, Nat. Biotechnol., 18(2):194-8 (2000).
Rothenberg et al., Oligodeoxynucleotides as anti-sense inhibitors of gene expression: therapeutic implications, J. Natl. Cancer Inst., 81(20):1539-44 (1989).
Takasaki et al., Structure-based design and characterization of exocyclic peptidomimetics that inhibit TNF alpha binding to its receptor, Nat. Biotechnol., 15(12):1266-70 (1997).
Wilson et al., In vitro selection of functional nucleic acids, Annu. Rev. Biochem., 68:611-47 (1999).
Wrighton et al., Increased potency of an erythropoietin peptide mimetic through covalent dimerization, Nat. Biotechnol., 15(12):1261-5 (1997).

APP/PS1-APP/PS1
(Isochronic)

APP/PS1-ASM+/-
(Heterochronic I)

APP/PS1-WT
(Heterochronic II)

COMPOSITION COMPRISING ASM INHIBITOR AS ACTIVE INGREDIENT FOR PREVENTING OR TREATING DEGENERATIVE NEUROLOGICAL DISORDERS

TECHNICAL FIELD

The present invention relates to a composition for preventing or treating degenerative neurological disorders, including an acid sphingomyelinase (ASM) inhibitor as an active ingredient.

BACKGROUND ART

Dementia refers to a progressive decline in memory and cognitive functioning that interferes with daily life, and may be largely divided into vascular dementia and Alzheimer's disease. Vascular dementia mainly corresponds to the case where stroke or cerebral infarction, etc. occurs by thrombus formed in blood vessels, and is known to be the onset of symptoms such as memory loss, etc. caused by damage to neighboring brain cells. On the other hand, Alzheimer's disease (AD), which accounts for a significantly greater part of dementia than vascular dementia, is a progressive brain disorder that slowly weakens memory, changes personality, and destroys thinking skills. Most patients of Alzheimer's disease die of pneumonia, etc. within 8 to 10 years. Worldwide, 3.5 to 10% of the elderly people over the age of 65 suffer from this disease, and there are an estimated 4 million patients only in the US. Social costs incurred to treat this disease reach US$100 billion every year only in the US, making Alzheimer's disease a signature disease of old age.

The pathogenesis of Alzheimer's disease known until now is liberating β-amyloid from amyloid precursor protein (APP), generating insoluble amyloid plaque by having the liberated β-amyloid cohered, causing degeneration of neural cells by cohesion of β-amyloid and generation of amyloid plaques, and inducing generation of secondary neurofibrillary tangle as a result. As such, it has been found out that the accumulation of β-amyloid in brain tissue and neural toxicity accompanied therefrom activate as very important causes of Alzheimer's disease, and accordingly, research is focused on substances, like BACE-1 inhibitor, that have an effect of inhibiting the generation of β-amyloid, inhibiting cohesion, or inhibiting toxicity, which having less side effects, over the world. β-amyloid is a fragment of amyloid precursor protein generated when APP, an amyloid precursor protein, receives proteolytic enzymes such as gamma-secretase and beta-secretase. The beta-secretase enzyme which plays the most important role in generating β-amyloid is generally referred to as BACE, and two types of BACE, i.e., BACE-1 and BACE-2, etc. are known. Among them, BACE-1 has most activity (about 90%) of beta-secretase, and thus is known to play a much more important role than BACE-2 in generating β-amyloid.

Also, according to recent epidemiologic studies, it has been reported that risk factors for cerebrovascular diseases such as high blood pressure, diabetes, hyperlipidemia and cardiac disorders have increased the occurrence of Alzheimer's disease as well as vascular dementia. From the modern medical point of view on cognitive impairment caused by Alzheimer's disease (AD), extensive degeneration and loss of cholinergic neurons in the brain are considered as the leading cause of cognitive decline, and as a means to overcome this problem, most studies aim to develop drugs that can partly recover impaired cognitive functioning by increasing the activity of the cholinergic nervous system left undamaged.

Recently, four drugs (tacrine, rivastigmine, donepezil, and galantamine) have been approved by the U.S. Food and Drug Administration (FDA) for the treatment of Alzheimer's disease, and they are all so-called acetylcholinesterase inhibitors which intend to dramatically improve cognitive functioning by inhibiting the activity of acetylcholinesterase enzymes. Until now, acetylcholinesterase inhibitors are the only drugs approved as a therapeutic agent of Alzheimer disease. However, these drugs have disadvantages such that they only present a temporary relief of symptoms in some Alzheimer's patients (40-50%), and the efficacy does not last long. Also, although the drug has to be taken for a long period of time due to the characteristic of the disease, the acetylcholinesterase inhibitors developed until now had problems such that they accompanied a number of side effects including liver toxicity. That is, the therapeutic agents developed until now only temporarily relieved the symptoms, and thus development of drugs fundamentally treating the disease or inhibiting the progress of the disease is urgently required.

Meanwhile, sphingolipid metabolism controls signal transduction of normal cells, and ASM, an enzyme controlling sphingolipid metabolism, is a protein expressed in almost all cell types, and has an important role in sphingolipid metabolism and membrane turnover. The ASM is mainly located within the endosomal/lysosomal compartment, and when there is a cellular stress response, it is transported outside the cell membrane. ASM increases in various diseases such as Wilson's disease, diabetes, cystic fibrosis, emphysema, etc., and may have a significant correlation with the onset of the diseases. However, despite the above role of ASM, currently there is little progress in studies on the relationship between ASM and Alzheimer's disease.

In this regard, the present inventors found ASM as a pathogenesis of Alzheimer's disease and completed the present invention by confirming that when ASM is partially removed in an Alzheimer's disease model mouse, that is when ASM is inhibited therein, such as when an Alzheimer's disease model mouse with a partial removal of ASM is in a parabionic union with an Alzheimer's disease model mouse, or when an Alzheimer's disease model mouse is injected with the serum of an Alzheimer's disease model mouse from which ASM gene has been removed, the deposition of β-amyloid in the brain tissue is inhibited and the ability to learn and remember is improved.

SUMMARY OF INVENTION

It is an object of the present invention to provide a composition for preventing or treating degenerative neurological disorders, including an ASM activity inhibitor or expression inhibitor as an active ingredient.

It is another object of the present invention to provide a method for preventing or treating degenerative neurological disorders, including administering to an individual a therapeutically effective amount of the composition.

It is yet another object of the present invention to provide a method for screening a substance for preventing or treating degenerative neurological disorders using the change in expression amount of ASM.

In order to achieve the above objects, the present invention provides a composition for preventing or treating degenerative neurological disorders, including an ASM activity inhibitor or expression inhibitor as an active ingredient.

Also, the present invention provides a method for preventing or treating degenerative neurological disorders, including administering to an individual a therapeutically effective amount of the composition.

Also, the present invention provides a method for screening a substance for preventing or treating degenerative neurological disorders, including treating a biological sample with a candidate substance, and measuring the change in expression amount of ASM.

According to the present invention, when ASM is partially removed in an Alzheimer's disease model mouse, that is when ASM is inhibited therein, such as when an Alzheimer's disease model mouse with a partial removal of ASM gene is in a parabionic union with an Alzheimer's disease model mouse, or when an Alzheimer's disease model mouse is injected with the serum of an Alzheimer's disease model mouse from which ASM gene has been removed, the deposition of β-amyloid in the brain tissue is inhibited and the ability to learn and remember is improved, and the present invention confirms such superb effects. Accordingly, ASM inhibitor may be effectively used to prevent or treat degenerative neurological disorders including Alzheimer's disease.

BEST MODE FOR CARRYING OUT THE INVENTION

Figure 1:
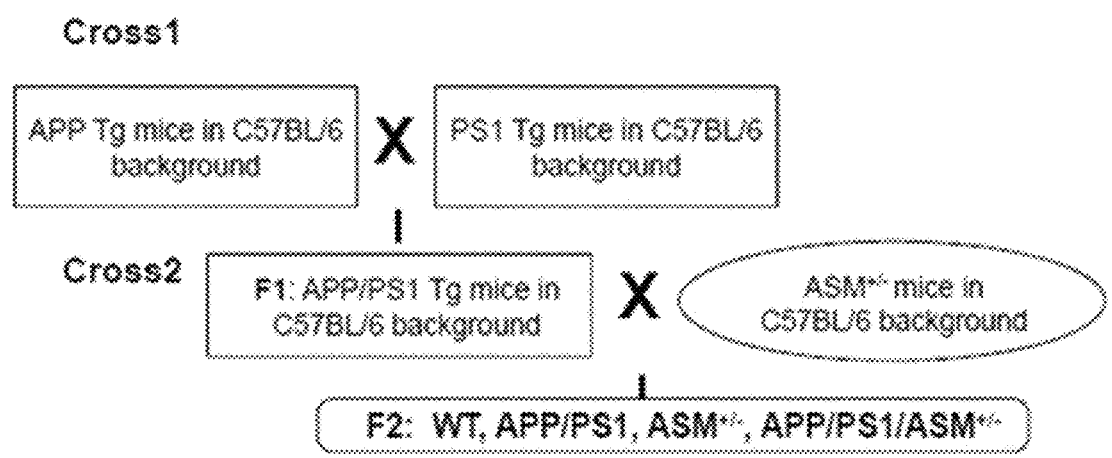
FIG. 1 is a view illustrating a process for manufacturing APP/PS1/ASM$^{+/-}$ mice.

Hereinafter, the present invention will be described in detail.

The present invention provides a composition for preventing or treating degenerative neurological disorders, including an ASM (acid sphingomyelinase) activity inhibitor or expression inhibitor as an active ingredient.

The composition includes a pharmaceutical composition or a food composition.

According to the present invention, when ASM is partially removed in an Alzheimer's disease model mouse, that is when ASM is inhibited therein, such as when an Alzheimer's disease model mouse with a partial removal of ASM gene is in a parabionic union with an Alzheimer's disease model mouse, or when an Alzheimer's disease model mouse is injected with the serum of an Alzheimer's disease model mouse from which ASM gene has been removed, the deposition of β-amyloid in the brain tissue is inhibited and the ability to learn and remember is improved, and the present invention confirms such superb effects. Accordingly, ASM inhibitor may be effectively used to prevent or treat degenerative neurological disorders including Alzheimer's disease.

The ASM activity inhibitor according to the present invention may be at least one selected from a group consisting of a compound, a peptide, a peptide mimetic, a substrate analogue, an aptamer, and an antibody, specifically binding to ASM protein, but is not limited thereto.

The peptide mimetics inhibit the binding domain of ASM protein, thus inhibiting the activity of ASM protein. The peptide mimetics may be peptides or non-peptides and may include amino acids linked by non-peptide bonds such as psi bonds (Benkirane, N., et al. J. Biol. Chem., 271:33218-33224, 1996). Moreover, the peptide mimetics may be "conformationally constrained" peptides, cyclic mimetics, or cyclic mimetics including at least one exocyclic domain, a link moiety (linking amino acid) and an active region. The peptide mimetics are constructed to resemble secondary structural features of Ubiquitin-Associated Protein 2 (UBAP2) and may mimic inhibitory features of macro molecules such as antibody (Park, B. W. et al. Nat Biotechnol 18, 194-198, 2000) or water soluble receptors (Takasaki, W. et al. Nat Biotechnol 15, 1266-1270, 1997). These peptides represent novel small molecule that may act with potency equivalent to the natural antagonist (Wrighton, N. C. et al. Nat Biotechnol 15, 1261-1265, 1997).

The aptamer is a single-stranded DNA or RNA molecule and may be obtained by isolating oligomers that bind to specific chemical molecules or biological molecules with high affinity and specificity by an evolutionary method using an oligonucleotide library called systematic evolution of ligands by exponential enrichment (SELEX) (C. Tuerand L. Gold, Science 249, 505-510, 2005; A. D. Ellington and J. W. Szostak, Nature 346, 818-822, 1990; M. Famulok, et. al., Acc. Chem. Res. 33, 591-599, 2000; D. S. Wilson and Szostak, Annu. Rev. Biochem. 68, 611-647, 1999). The aptamer may specifically bind to a target to regulate its activity and may inhibit the function of the target by binding, for example.

The antibody specifically and directly binds to the ASM to effectively inhibit its activity. Preferably, a polyclonal antibody or monoclonal antibody may be used as the antibody that specifically binds to the ASM. The antibody that specifically binds to the ASM may be prepared by a method known to those skilled in the art, and a commercially available ASM antibody may be purchased and used. The antibody may be prepared by injecting the ASM protein as an immunogen into an external host according to a conventional method known to those skilled in the art. The external host may include mammals such as mice, rats, sheep, rabbits, etc. The immunogen may be injected intramuscularly, intraperitoneally, or subcutaneously, and generally may be injected with an adjuvant to enhance antigenicity. Blood samples may be taken from the external host at regular intervals and serum exhibiting titer and specificity to the antigen may be collected to separate an antibody therefrom.

The ASM expression inhibitor according to the present invention may be at least one selected from a group consisting of an antisense nucleotide, small hairpin RNA (shRNA), small interfering (siRNA) and ribozyme, complementarily binding to mRNA of an ASM gene or a gene promoting expression of ASM, but is not limited thereto.

The siRNA is composed of a sense sequence of 15 to 30-mers selected from the mRNA sequence of a gene that encodes the ASM protein and an antisense sequence complementarily binding to the sense sequence. Here, preferably, the sense sequence may be composed of about 25 nucleotides, but is not particularly limited thereto.

As defined by Watson-Crick base pairs, the antisense nucleotide is hybridized with a complementary sequence of DNA, immature-mRNA or mature-mRNA to interrupt the transmission of genetic information as a protein in DNA. A target sequence specific antisense nucleotide is exceptionally multi-functional. The antisense nucleotide is a long chain of monomers, which favors hybridization to a target RNA sequence. Numbers of reports have recently been made to prove the utility of an antisense nucleotide as a biochemical tool in study of a target protein (Rothenberg et al., J. Natl. Cancer Inst., 81:1539-1544, 1999). Great progress has been made in the fields of oligonucleotide chemistry and nucleotide synthesis having improved cell adhesion of oligonucleotide, target binding affinity and resistance against nuclease, suggesting that an antisense nucleotide might be considered a new form of an inhibitor.

The degenerative neurological disorder according to the present invention includes Alzheimer's disease, Parkinson's disease, progressive supranuclear palsy, multiple system atrophy, olivopontocerebellar atrophy (OPCA), Shy-Drager syndrome, Striatonigral degeneration, Huntington's disease, Amyotrophic lateral sclerosis (ALS), essential tremor, cortico-basal ganglionic degeneration, diffuse Lewy body disease, Parkinson-ALS-dementia complex of Guam, Pick's disease, ischemia, and cerebral infarction, but is not limited thereto.

The composition of the present invention may include, together with the ASM activity inhibitor or expression inhibitor, at least one of a known active ingredient having an effect of inhibiting ASM expression or activity, or a known active ingredient having an effect of treating degenerative neurological disorders.

Also, the pharmaceutical composition of the present invention may be administered orally or parenterally (e.g., applied intravenously, subcutaneously, intraperitoneally or topically) according to the intended use, and the dosage may vary according to a patient's weight, age, gender, health condition, diet, administration time, administration method, administration period or interval, excretion rate, constitutional specificity, nature of formulation, etc. The dosage of the ASM expression inhibitor or activity inhibitor of the present invention is about 0.001 to 1000 mg/kg per day, preferably about 0.1 to 500 mg/kg per day, but this may vary depending on the clinical test result. Preferably, the pharmaceutical composition of the present invention may be administered once or several times a day.

The pharmaceutical composition of the present invention may be formulated in a variety of formulations for administration. The excipients that may be included in the present invention are non-toxic inert pharmaceutically suitable solid, semi-solid or liquid formulation auxiliaries of any type, for example, fillers, weighting agents, binders, wetting agents, disintegrating agents, dispersing agents, surfactants or diluents, etc.

The pharmaceutical composition of the present invention may be formulated in the form of tablets, coated tablets, capsules, pills, granules, suppositories, solutions, suspensions and emulsions, pastes, ointments, gels, creams, lotions, powders or sprays.

The composition of the present invention may be added to dietary supplements for the improvement of degenerative neurological disorders. When using the ASM expression inhibitor or activity inhibitor of the present invention as a food additive, the active ingredient may be added as it is or together with other food or food ingredients, and it may be suitably used according to a conventional manner. The amount of active ingredient added may be determined properly according to the purpose of use (preventive, health or therapeutic purposes). In general, when manufacturing food or beverage, the active ingredient of the present invention is added in an amount of 15% by weight or less to the raw material, preferably in an amount of 10% by weight or less. However, for health and hygiene purposes, or for long-term intake for the purpose of health control, the amount of active ingredient may be equal to or less than the above range, and since there is no problem in terms of safety, the active ingredient may be used in an amount greater than or equal to the above range.

There is no particular limitation in the type of food. Examples of the food to which this substance may be added include meat, sausages, bread, chocolate, candies, snacks, confectionery, pizza, ramen, other noodles, gum, dairy products including ice cream, soup, beverages, tea, drinks, alcohol drinks, and vitamin complexes, etc. That is, food may comprise all kinds of dietary supplements in the conventional sense.

The health beverage composition of the present invention may include additional ingredients such as various flavoring agents or natural carbohydrates, etc., like other beverages. The natural carbohydrates above may be monosaccharides such as glucose and fructose, disaccharides such as maltose and sucrose, polysaccharides such as dextrin and cyclodextrin, and sugar alcohols such as xylitol, sorbitol and erythritol, etc. Natural sweeteners such as thaumatin and *stevia* extract, and synthetic sweeteners such as saccharin and aspartame, etc. may be used as sweeteners. The ratio of natural carbohydrate is generally in the range of about 0.01 to 0.20 g per 100 g of the composition of the present invention, and preferably in the range of about 0.04 to 0.10 g.

In addition to the above, the composition of the present invention may include various nutrients, vitamins, electrolytes, flavoring agents, coloring agents, pectic acid and its salts, alginic acid and its salts, organic acid, protective colloidal thickeners, pH adjusting agents, stabilizers, preservatives, glycerin, alcohol, carbonating agents used in carbonated beverages, etc. Further, the composition of the present invention may include pulp for the production of natural fruit juice, fruit juice beverage and vegetable beverage. These ingredients may be used independently or in combination with other ingredients. The ratio of the additive is not so important but is generally selected from a range of 0.01 to 0.20 parts by weight with respect to 100 parts by weight of the composition of the present invention.

Also, the present invention provides a method for preventing or treating degenerative neurological disorders, including administering to a subject a therapeutically effective amount of the composition.

It is obvious to those skilled in the art that the therapeutically effective amount may be determined within the scope of sound medical judgment. Preferably, the specific therapeutically effective amount for a particular patient may vary depending on a variety of factors including the type and degree of a desired reaction, the specific composition including the use of any other agents according to the intended use, the patient's age, weight, general health condition, gender, diet, administration time, administrate route and excretion rate of the composition, duration of treatment, other drugs used in combination or coincidentally with the specific composition, and like factors well known in the medical arts. Therefore, preferably, the effective amount of the composition suitable for the purpose of the present invention is determined in consideration of the foregoing.

In addition, optionally, the composition of the present invention may be administered in combination with a known therapeutic agent for degenerative neurological disorders to increase the effect of treating degenerative neurological disorders.

The present invention is applicable to any mammal with a degenerative neurological disorder. Here, mammals include human, primates, and livestock animals such as cows, pigs, sheep, horses, dogs, cats, etc.

Also, the present invention provides a method for screening a substance for preventing or treating degenerative neurological disorders, including 1) treating a biological sample with a candidate substance, and 2) measuring the change in expression amount of mRNA or protein of ASM (acid sphingomyelinase) from the biological sample in step 1).

The biological sample in the step 1) may include blood, urine, saliva or tissue, etc. of animals with degenerative neurological disorders, but is not limited thereto.

The method for measuring the change in expression amount of mRNA in the step 2) includes reverse transcription polymerase chain reaction (RT-PCR), competitive RT-PCR, realtime RT-PCR, RNase protection assay (RPA), Northern blotting, and DNA chip, etc., but is not limited thereto.

The method for measuring the change in expression amount of protein in the step 2) includes Western blotting, enzyme linked immunosorbent assay (ELISA), radioimmunoas say (RIA), radioimmunodiffusion, Ouchterlony immunodiffusion, rocket immunoelectrophoresis, immunohistostaining, immunoprecipitation assay, complement fixation assay, fluorescence activated cell sorter (FACS) and protein chip, etc., but is not limited thereto.

Hereinafter, preferred Examples will be provided to facilitate understanding of the present invention. However, the following Examples are provided for better understanding of the present invention only, and the scope of the present invention is not limited by the following Examples.

[Example 1] Confirmation on the Effect of ASM Inhibition on the Treatment of Alzheimer's Disease in ASM (Acid Sphingomyelinase) Mutant Mice 1. Preparation of ASM Mutant Mice An experiment was conducted using APP/PS1 (APP/presenilin) double mutant mice and APP/PS1/ASM$^{+/-}$ triple mutant mice (with partial genetic removal of ASM), which are test animal models of Alzheimer's disease.

The animal test conducted was approved by the Kyungpook National University Institutional Animal Care and Use Committee (IACUC). Transgenic mouse lines overexpressing APPswe (hAPP695swe) or PS1 (presenilin-1M146V) mutations were used onto C57BL/6 mice (Charles River, UK) [hereinafter, APP mice: mice overexpressing APPswe, PS1 mice: overexpressing presenilin-1M146V; GlaxoSmithKline]. ASM$^{+/-}$ mice (only one of a pair of ASM genes is removed) were crossed with APP/PS1 mice to prepare APP/PS1/ASM$^{+/-}$ mice. Detailed process is illustrated in FIG. 1.

2. Confirmation on ASM Concentration Level in ASM Mutant Mice

The ASM concentration levels were measured in the plasma, brain tissue and fibroblast of nine-month old wild type (WT) mice, APP/PS1 mice and APP/PS1/ASM$^{+/-}$ mice prepared in Example 1-1. More specifically, 3 µl of plasma, brain tissue and fibroblast samples from each mouse were mixed with an ASM activity buffer, and stored at 37° C. The hydrolysis reaction was completed by adding 114 µl of ethanol to the mixed solution, and then the mixed solution was centrifuged. 30 µl of the supernatant was transferred into a glass vial, and then 5 µl was applied to the UPLC system. The ASM concentration level was quantified in comparison with a bodipy (aminoacetaldehyde) combined with sphingomyelin and ceramide. The sphingomyelin and ceramide levels were extracted and quantified according to a known method, by extracting lipid from the sample, resuspending the dried lipid extract in 25 µl of 0.2% Igepal CA-630 (Sigma-Aldrich), and quantifying the concentration level of each lipid using the UPLC system. The results are illustrated in FIG. 2 (left: plasma; middle: brain tissue; right: fibroblast).

Figure 2:
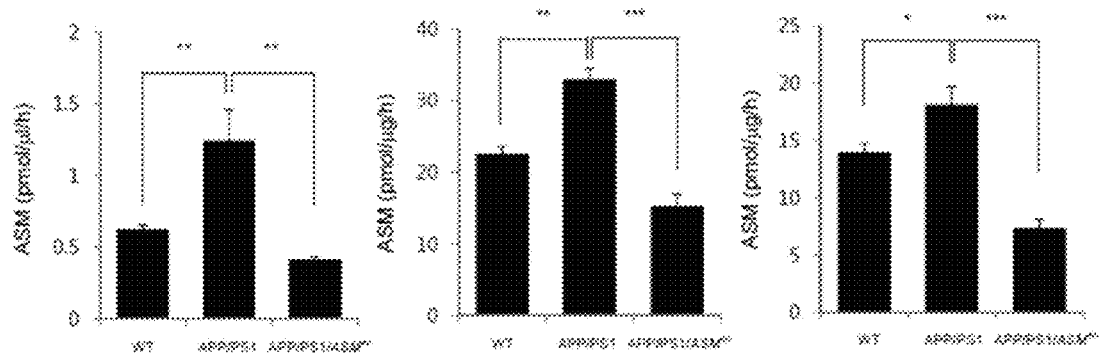
FIG. 2 is a view illustrating the ASM concentration levels in the plasma, brain tissue and fibroblast of Alzheimer's disease model mice (APP/PS1) and mice with partial removal of ASM in the Alzheimer's disease model mice (APP/PS1/ASM$^{+/-}$) (left: plasma; middle: brain tissue; right: fibroblast)

As illustrated in FIG. 2, it is confirmed that the ASM concentration levels in the plasma, brain tissue and fibroblast of APP/PS1/ASM$^{+/-}$ mice decreased remarkably, as compared to the ASM concentration levels in the plasma, brain tissue and fibroblast of APP/PS1 mice.

3. Confirmation on Inhibition of Deposition of β-Amyloid in Brain Tissue of ASM Mutant Mice As confirmed in Example 1-2, in order to confirm how the decrease in ASM concentration level in APP/PS1/ASM$^{+/-}$ mice affects Alzheimer's disease in a pathological aspect, the deposition level of β-amyloid in the brain tissue was analyzed.

First, the cerebral cortex and hippocampus tissue of each mouse prepared in Example 1-1 were isolated, and then a tissue fragment was obtained and this was dyed with thioflavin S according to a conventional known method. The results are illustrated in FIG. 3 (cerebral cortex) and FIG. 4 (hippocampus).

Figure 3:
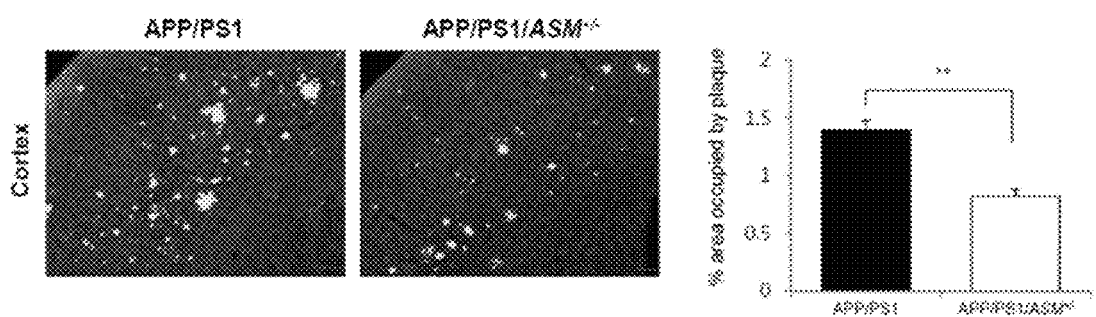
FIG. 3 is a view confirming the deposition of β-amyloid in the cerebral cortex in the brain tissues of APP/PS1 mice and APP/PS1/ASM$^{+/-}$ mice using thioflavin S dye.
Figure 4:
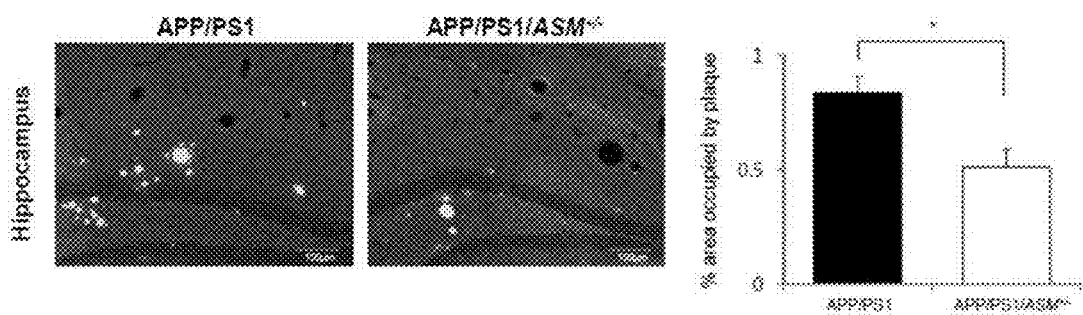
FIG. 4 is a view confirming the deposition of β-amyloid in the hippocampus in the brain tissues of APP/PS1 mice and APP/PS1/ASM$^{+/-}$ mice using thioflavin S dye.

As illustrated in FIG. 3 and FIG. 4, it is confirmed that Aβ40 and Aβ42 deposited in the brain tissue of APP/PS1/ASM$^{+/-}$ mice decreased remarkably, as compared to the brain tissue of APP/PS1 mice.

Also, immunofluorescence was performed according to a conventional known method using anti-20G10 (mouse, 1:1000) antibody against Aβ42, anti-G30 (rabbit, 1:000) antibody against Aβ40, anti-Iba-1 (rabbit, 1:500, Wako) antibody, anti-GFAP (rabbit, 1:500, DAKO) antibody and anti-activity caspase3 (rabbit, 1:50, Chemicon) antibody. Tissue fragments were observed using a confocal laser scanning microscope equipped with Fluoview SV1000 imaging software (Olympus FV1000, Japan) or an Olympus BX51 microscope, and the percentage of the area of the dyed area with respect to the area of the entire tissue was quantified using Metamorph software (Molecular Devices).

Also, β-amyloid deposition was confirmed using commercially available ELISA kits (Biosource). More specifically, hemispheres of the brain of each mouse were homogenized in a buffer containing 0.02 M of guanidine. Thereafter, ELISA was performed for Aβ340 and Aβ342 according to the manufacturer's instructions.

Figure 5:
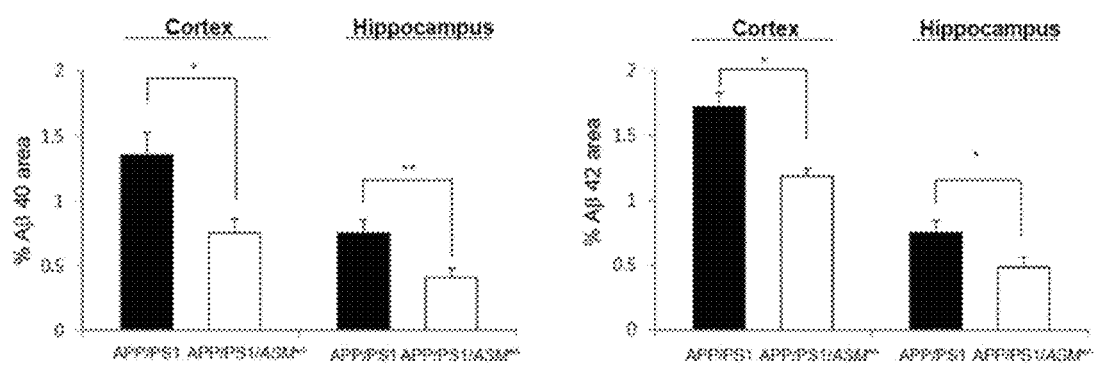
FIG. 5 is a view confirming the deposition of β-amyloid in the brain tissues of APP/PS1 mice and APP/PS1/ASM$^{+/-}$ mice using immunofluorescence.
Figure 6:
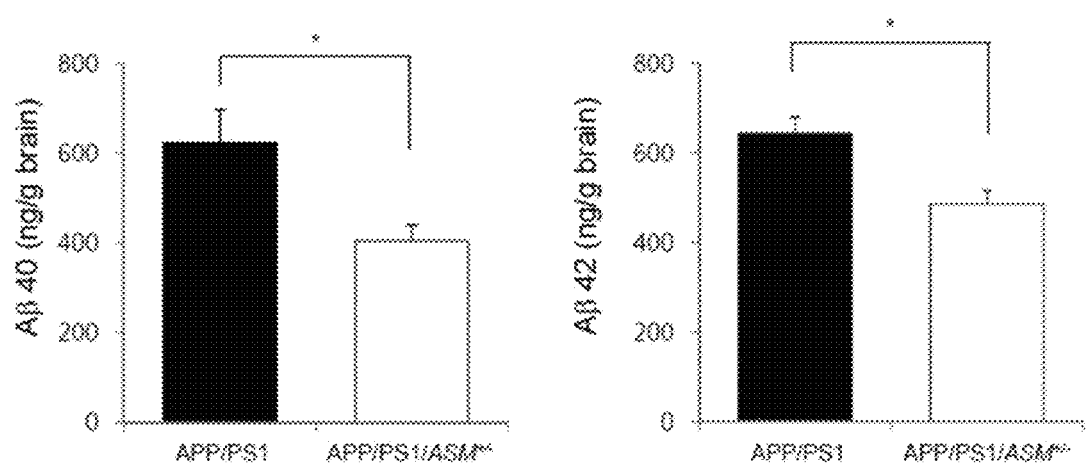
FIG. 6 is a view confirming the deposition of β-amyloid in the brain tissues of APP/PS1 mice and APP/PS1/ASM$^{+/-}$ mice using ELISA.

The results are illustrated in FIG. 5 (immunofluorescence) and FIG. 6 (ELISA).

As illustrated in FIG. 5 and FIG. 6, it is confirmed that Aβ40 and Aβ42 deposited in the brain tissue of APP/PS1/ASM$^{+/-}$ mice decreased remarkably, as compared to the brain tissue of APP/PS1 mice.

4. Confirmation on Improvement of Ability to Learn and Remember in ASM Mutant Mice In order to confirm the effect of improving the ability to learn and remember in APP/PS1/ASM$^{+/-}$ mice prepared in Example 1-1, a Morris water maze (MWM) test was performed according to a conventional known method.

More specifically, wild type mice, APP/PS1/ASM$^{+/-}$ mice, ASM$^{+/-}$ mice and APP/PS1 mice were used. The mice were given four trials per day for 10 days to learn the task, and on day 11, the mice were given a probe trial in which the platform was removed. The escape latency during the test period and the time spent in the target platform on day 11 were measured. The results are illustrated in FIG. 7 and FIG. 8.

Figure 7:
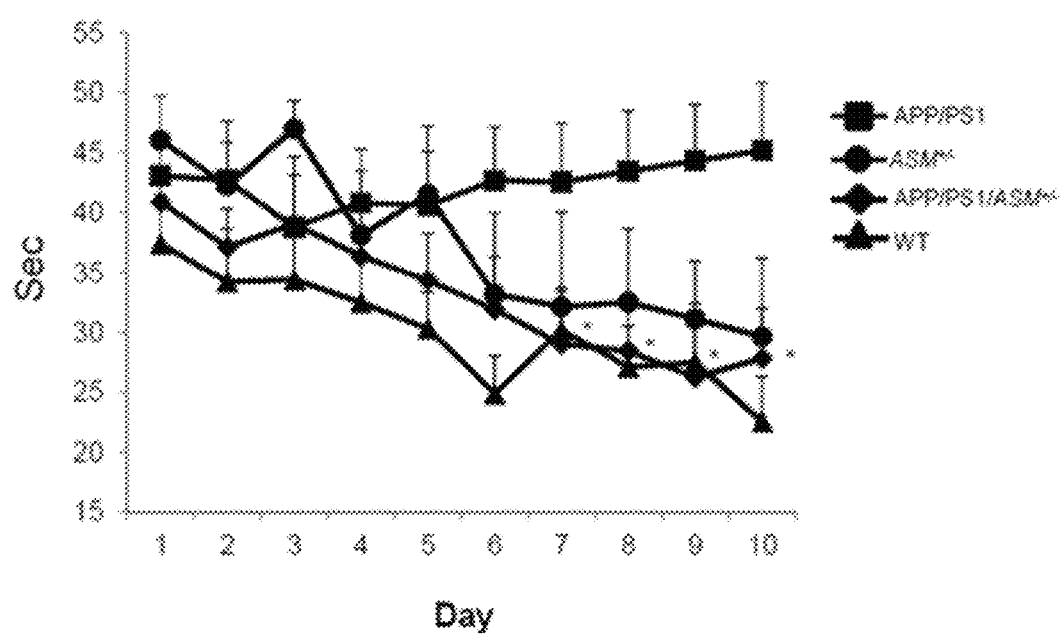
FIGS. 7 and 8 are views confirming the effect of improving the ability to learn and remember of APP/PS1/ASM$^{+/-}$ mice using Morris water maze (MWM) test.
Figure 8:
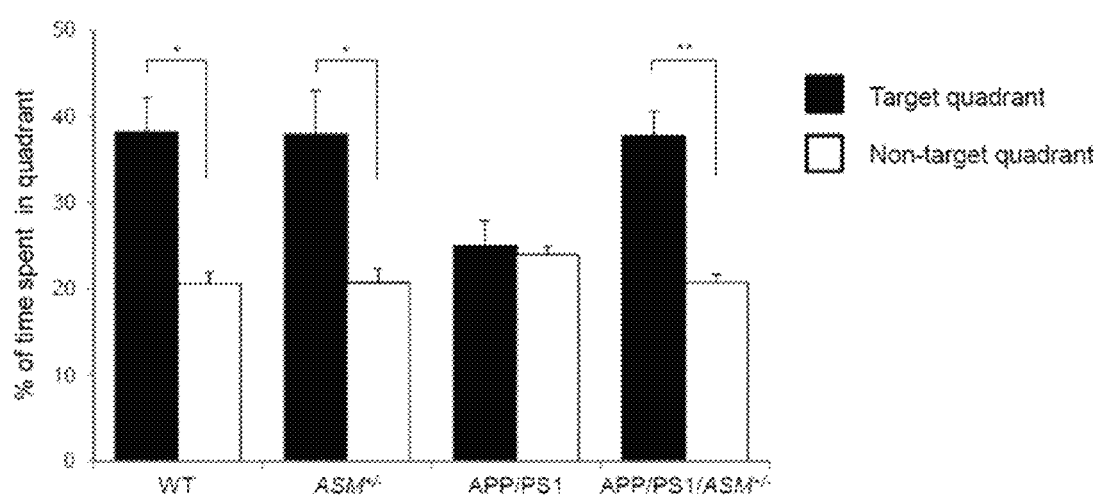

As illustrated in FIG. 7 and FIG. 8, APP/PS1 mice did not show any change in escape latency during the test period, and did not show any difference in the time spent in the target platform and non-target platform, and thus it is confirmed that APP/PS1 mice showed disorder in forming spatial memory. In comparison, it is confirmed that APP/PS1/ASM$^{+/-}$ mice presented improved ability to learn and remember to a level similar to wild type mice.

In order to verify the MWM test results, a fear conditioning test was performed, which evaluates the ability to learn and remember by combining environmental context or conditioned stimulus with electric shock according to a conventional known method.

More specifically, wild type mice, APP/PS1/ASM$^{+/-}$ mice, ASM$^{+/-}$ mice and APP/PS1 mice were used. On day 1 of the test, each mouse was individually placed into a conditioned chamber, and then after a 60-second exploratory period, a tone (10 kHz, 70 dB) was delivered for 10 seconds. This served as the conditioned stimulus (CS). The CS was coterminated with the unconditioned stimulus (US), an electrical footshock (0.3 mA, 1 s). The CS-US pairing was delivered twice at a 20-second intertrial interval. On day 2, each mouse was placed in the fear-conditioning chamber containing the same exact context, but without administration of a CS or footshock. Freezing was observed for 5 minutes. On day 3, each mouse was placed in a test chamber that was different from the conditioning chamber. After a 60-second exploratory period, the tone was presented for 60 seconds without the footshock. Freezing was measured to measure fear memory. The results are illustrated in FIG. 9 and FIG. 10.

Figure 9:
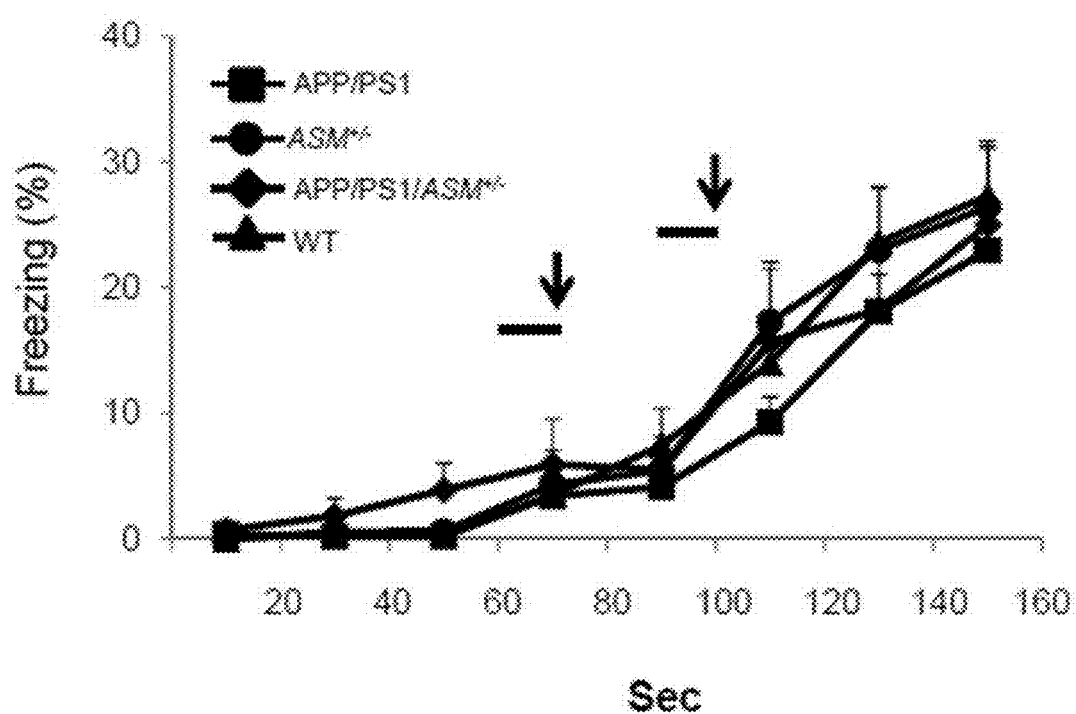
FIGS. 9 and 10 are views confirming the effect of improving the ability to remember of APP/PS1/ASM$^{+/-}$ mice using fear conditioning test.
Figure 10:
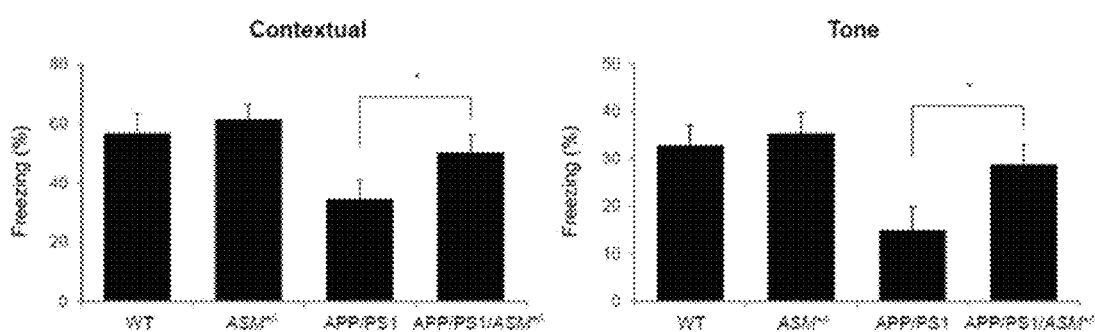
Figure 11:
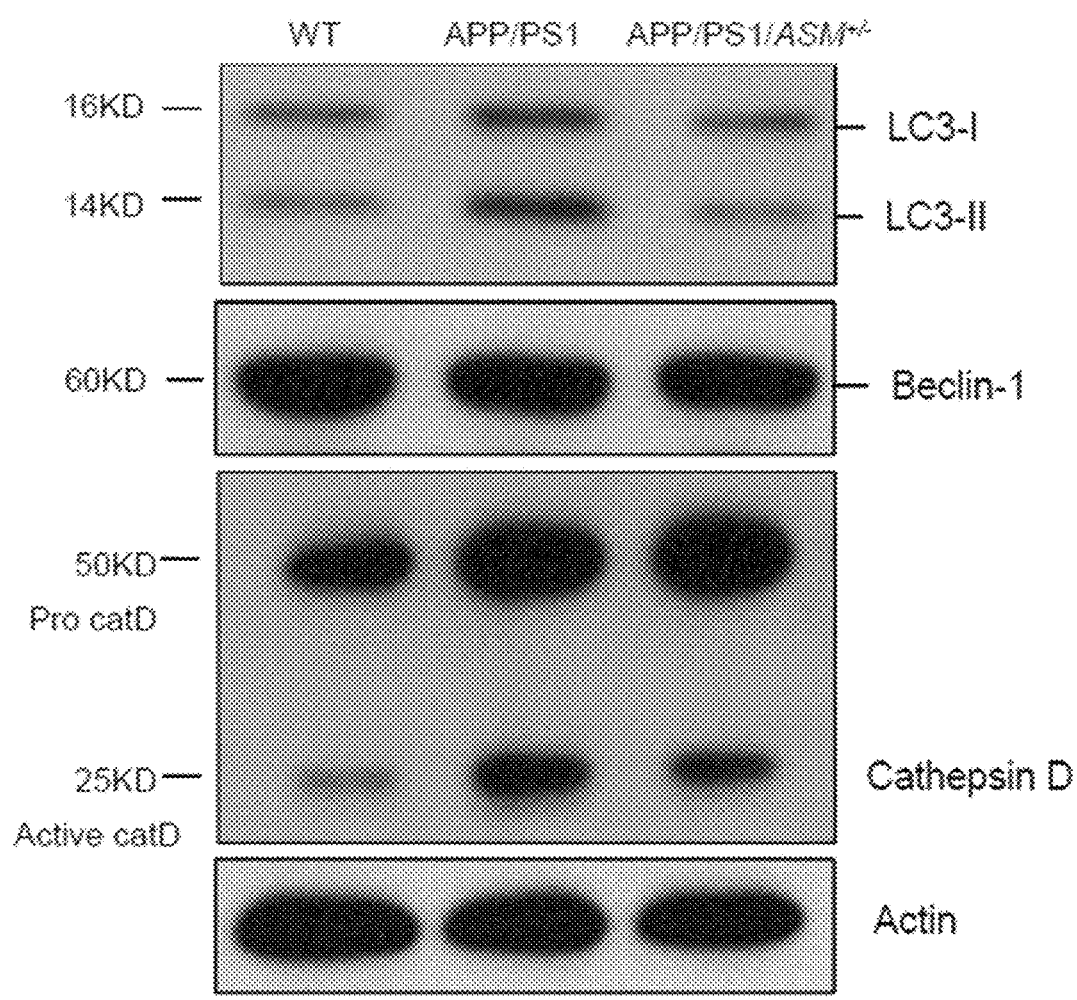
FIG. 11 is a view confirming the expression level of autophagy-related protein in the tail fibroblast from WT mice, APP/PS1 mice and APP/PS1/ASM$^{+/-}$ mice using Western blotting.
Figure 12:
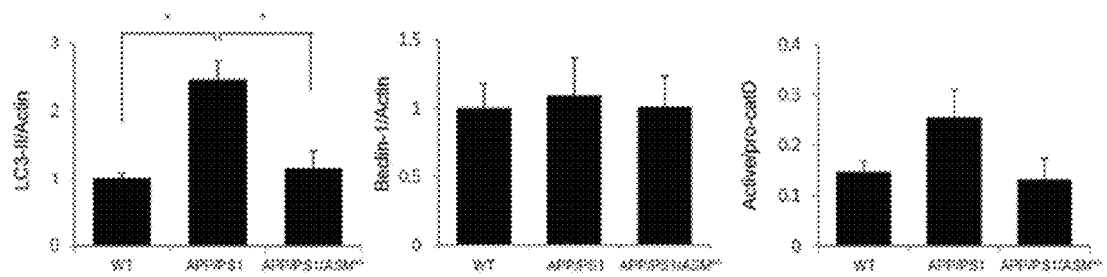
FIG. 12 is a view confirming the expression level of autophagy-related protein in the tail fibroblast from WT mice, APP/PS1 mice and APP/PS1/ASM$^{+/-}$ mice using densitometric quantification.
Figure 13:
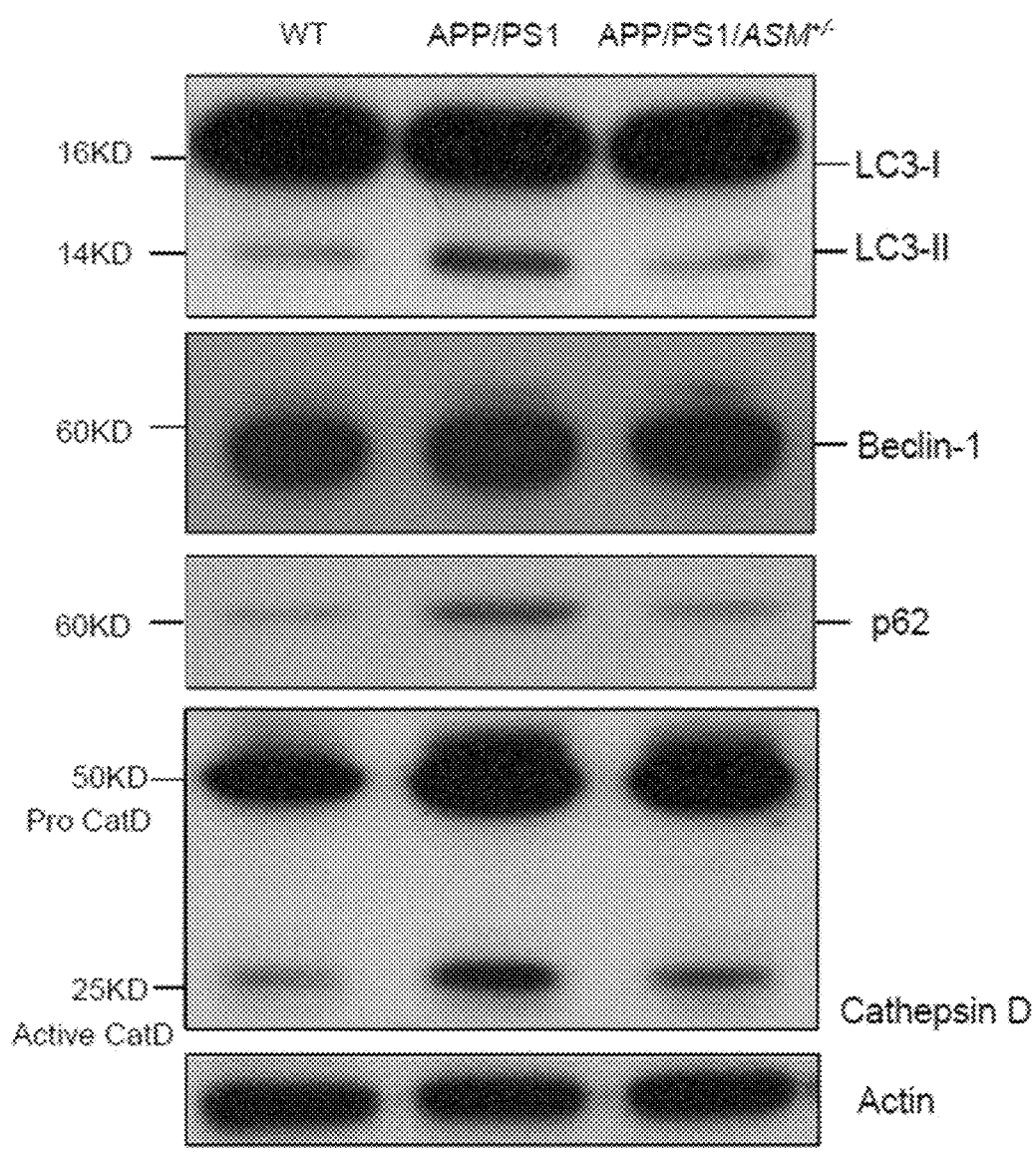
FIG. 13 is a view confirming the expression level of autophagy-related protein in the brain tissues of WT mice, APP/PS1 mice and APP/PS1/ASM$^{+/-}$ mice using Western blotting.
Figure 14:
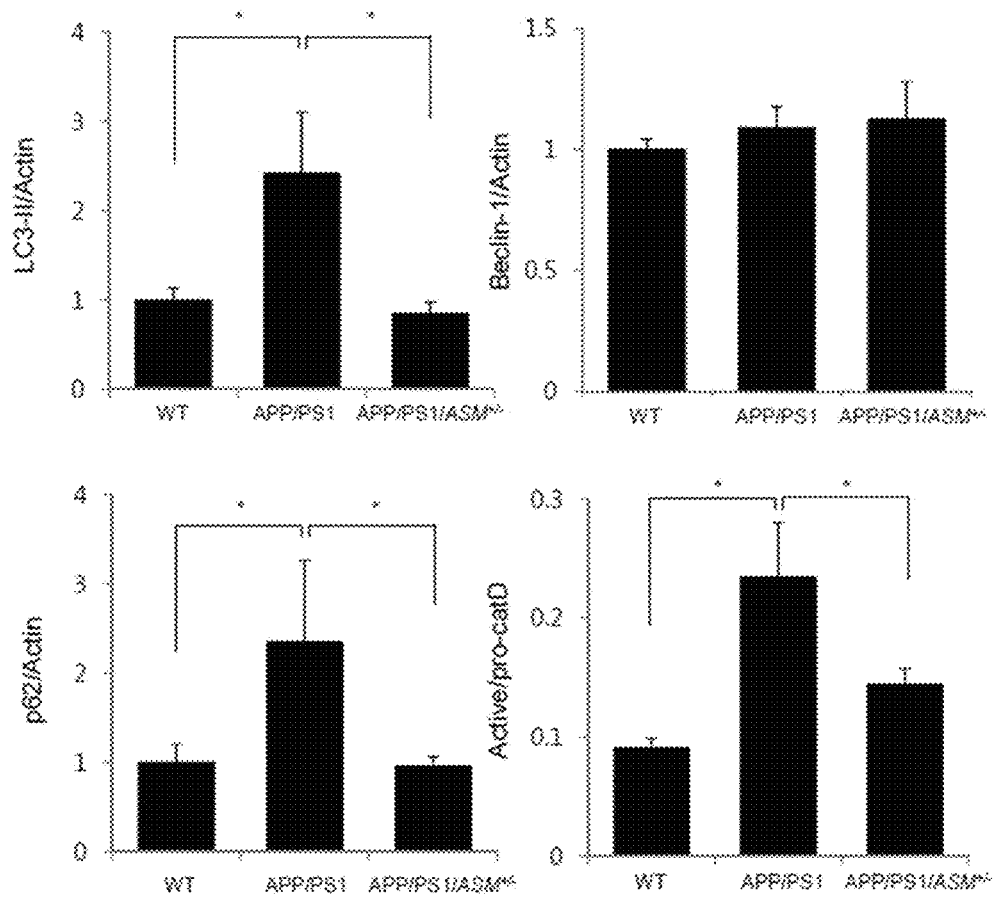
FIG. 14 is a view confirming the expression level of autophagy-related protein in the brain tissues of WT mice, APP/PS1 mice and APP/PS1/ASM$^{+/-}$ mice using densitometric quantification.

As illustrated in FIG. 9 and FIG. 10, it is confirmed that APP/PS1/ASM$^{+/-}$ mice has improved ability to remember than APP/PS1 mice.

[Example 2] Confirmation on Effect of ASM Inhibition on Autophagy in ASM (Acid Sphingomyelinase) Mutant Mice 1. Confirmation on Autophagy-Related Gene Expression by ASM Inhibition In order to confirm the activation of genetic ASM inhibition on autophagy-related pathways of Alzheimer's disease, the tail fibroblast and brain tissue samples from nine-month old wild type mice, APP/PS1 mice and APP/PS1/ASM$^{+/-}$ mice prepared in Example 1-1 were analyzed.

More specifically, Western blotting was performed according to a conventional known method using LC3 (rabbit, 1:1000, Cell Signaling Technologies, 4108S), Beclin-1 (rabbit, 1:1000, Cell Signaling Technologies, 3738S), p62 (rabbit, 1:1000, Cell Signaling Technologies, 5114S), cathepsin D (goat, 1:500, R&D Systems, BAF1029) and β-actin (1:1000, Santa Cruz, S.C.-1615) antibodies, and densitometric quantification was performed using ImageJ software (US National Institutes of Health). The results are illustrated in FIGS. 11 to 14.

As illustrated in FIGS. 11 to 14, it is confirmed that the conversion from LC3-I to LC3-II increased in APP/PS1 mice as compared to WT mice, and that the expression of increased LC3-II decreased in APP/PS1/ASM$^{+/-}$ mice. Beclin-1 expression did not significantly vary between the groups. Also, the expression of cathepsin D (lysosomal hydrolase) and p62, which are indicators of autophagic turnover, increased in Alzheimer's patients, and thus this is paralogically related to Alzheimer's disease. However, it is confirmed that the expression of cathepsin D and p62 increased in APP/PS1 mice and the increased expression of cathepsin D and p62 decreased in APP/PS1/ASM$^{+/-}$ mice, as compared to WT mice.

2. Evaluation on Proteolytic Activity by ASM Inhibition

The proteolytic activity in the tail fibroblast from nine-month old wild type mice, APP/PS1 mice and APP/PS1/ASM$^{+/-}$ mice prepared in Example 1-1 were confirmed.

In order to label long-lived proteins, pulse-chase experiment was performed by giving a pulse with [$^3$H]-leucine (2 μCi/ml) for 48 hours. Labeled cells were washed, and cultured in a complete medium of an environment inhibiting autophagy or a serum starvation medium inducing autophagy. Aliquots of the medium were collected at different time period and precipitated with 10% TCA, and then they were filtered with a film having holes of 0.22 μm and the radioactivity was measured to analyze proteolytic activity. The results are illustrated in FIG. 15.

Figure 15:
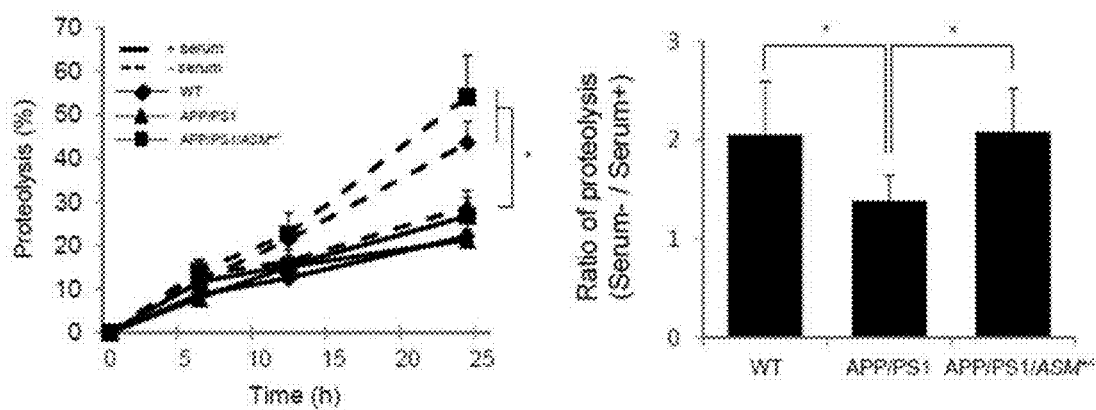
FIG. 15 is a view confirming the proteolytic activity in the tail fibroblast from WT mice, APP/PS1 mice and APP/PS1/ASM$^{+/-}$ mice.

As illustrated in FIG. 15, when autophagy (culturing in serum starvation medium) is induced, it is confirmed that proteolytic activity increased in cells derived from APP/PS1/ASM$^{+/-}$ mice, as compared to cells derived from WT mice.

3. Analysis on Mouse Brain Tissue Using Transmission Electron Microscope (TEM)

The brain tissues of nine-month old wild type mice, APP/PS1 mice and APP/PS1/ASM$^{+/-}$ mice prepared in Example 1-1 were fixed in 3% glutaraldehyde containing phosphate buffer, 0.1M, pH 7.4, and postfixed in Sorensen's phosphate buffer containing osmium tetroxide. After dehydration with ethyl alcohol, the tissues were embedded in Epon (Electron Microscopy Sciences). They were cut serially and analyzed using Transmission Electron Microscope (Tecnai). Images were captured on a digital camera and Xplore3D tomography software. The results are illustrated in FIG. 16.

Figure 16:
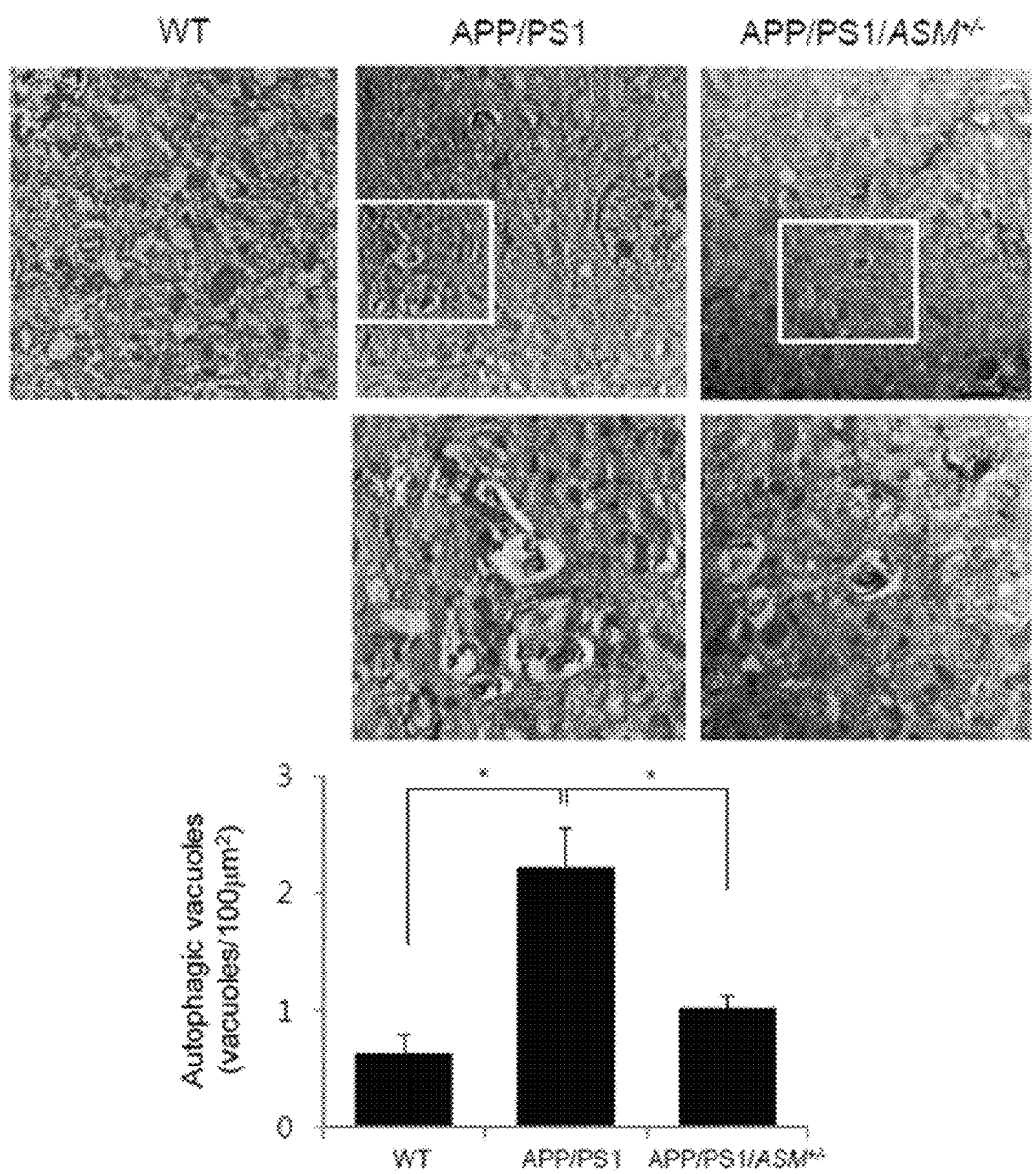
FIG. 16 is a view observing the brain tissues of WT mice, APP/PS1 mice and APP/PS1/ASM$^{+/-}$ mice using transmission electron microscope (TEM)

As illustrated in FIG. 16, it is confirmed that the size and number of autophagic vacuole (AV) increased in the brain tissue of APP/PS1 mice, and the size and number of vacuole in the brain tissue of APP/PS1/ASM$^{+/-}$ mice were observed to be slightly greater than those in WT mice, but smaller than those in APP/PS1 mice.

[Example 3] Confirmation on Effect of ASM Inhibition on Autophagy in Human Cell

1. Confirmation on Change in Autophagy-Related Gene Expression by Recombinant ASM Protein in Human Fibroblast Human fibroblast acquired from the Coriell Institute, and was cultured in DMEM medium containing 15% FBS at 37° C. and 5% of $CO_2$. The cell lines were treated with recombinant ASM (1 μM to 10 μM), and then Western blotting and densitometric quantification were performed in the same manner as Example 2-1. The results are illustrated in FIG. 17 and FIG. 18.

Figure 17:
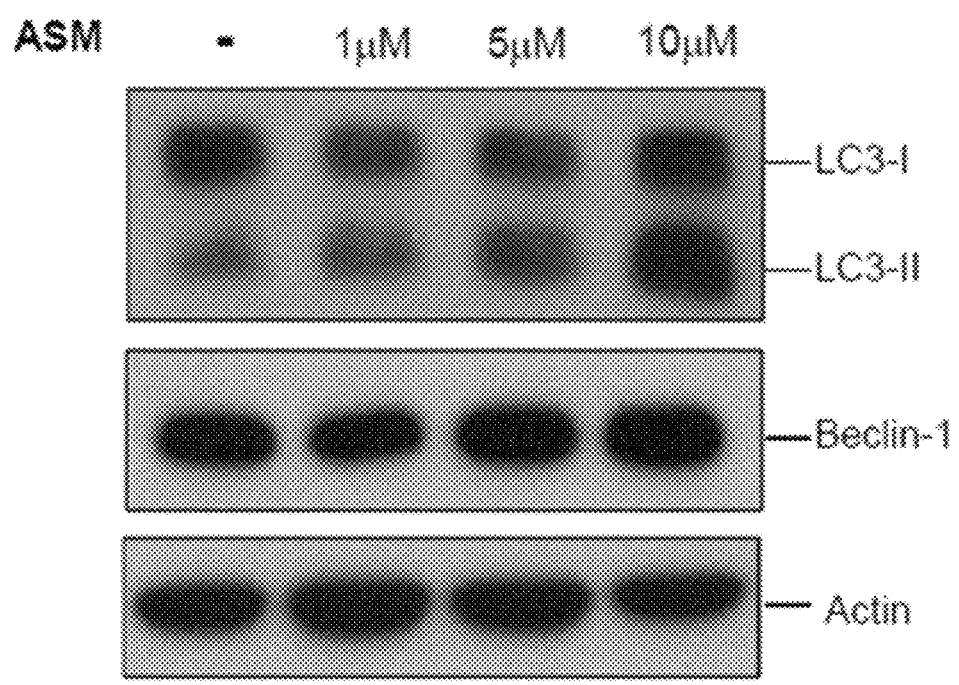
FIG. 17 is a view confirming the expression level of autophagy-related protein when treating human fibroblast with ASM (1 μM to 10 μM) using Western blotting.
Figure 18:
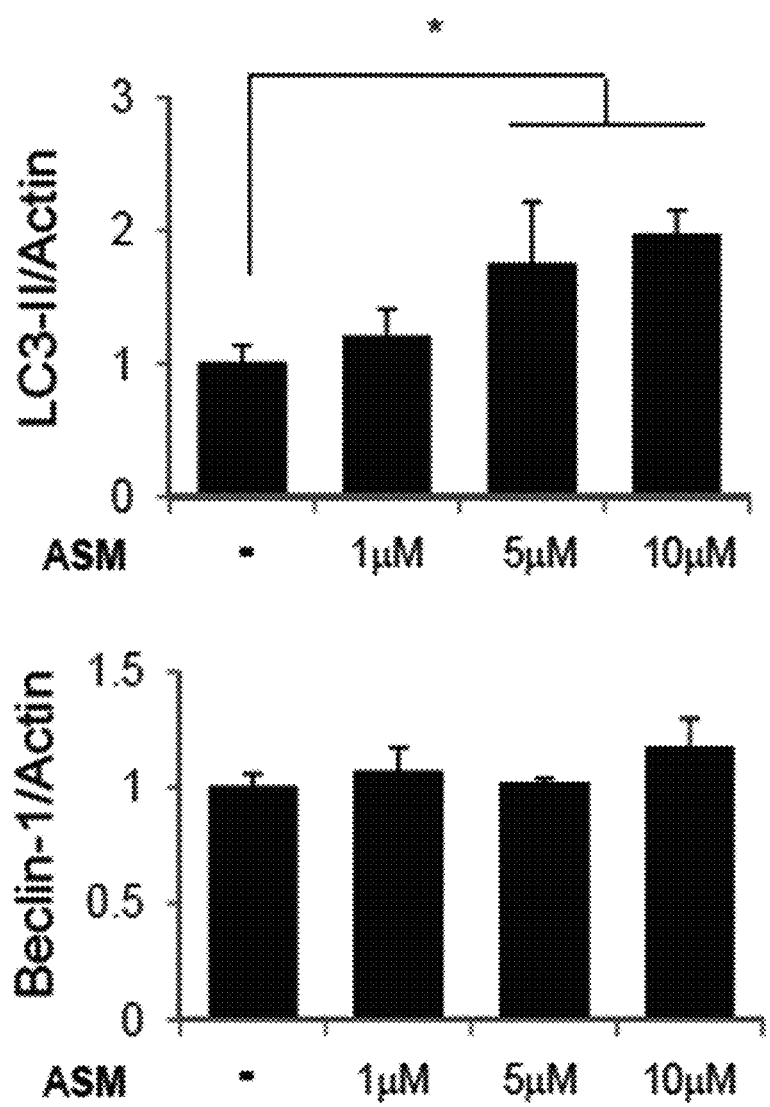
FIG. 18 is a view confirming the expression level of autophagy-related protein when treating human fibroblast with ASM (1 μM to 10 μM) using densitometric quantification.

As illustrated in FIG. 17 and FIG. 18, it is confirmed that conversion from LC3-I to LC3-II takes place depending on the concentration of recombinant ASM treatment, and there is no significant change in expression of beclin-1.

2. Confirmation on Mechanism of ASM Using M6P (Mannose-6-Phosphate)

In order to confirm how ASM affects autophagosome, a test was conducted as follows. Human fibroblast was treated with ASM alone, or treated in the presence of mannose-6-phosphate (M6P; 10 mM) relating to the activation of placing protein in lysosome, and then the accumulation of autophagosome was confirmed using Western blotting and densitometric quantification. The results are illustrated in FIG. 19.

Figure 19:
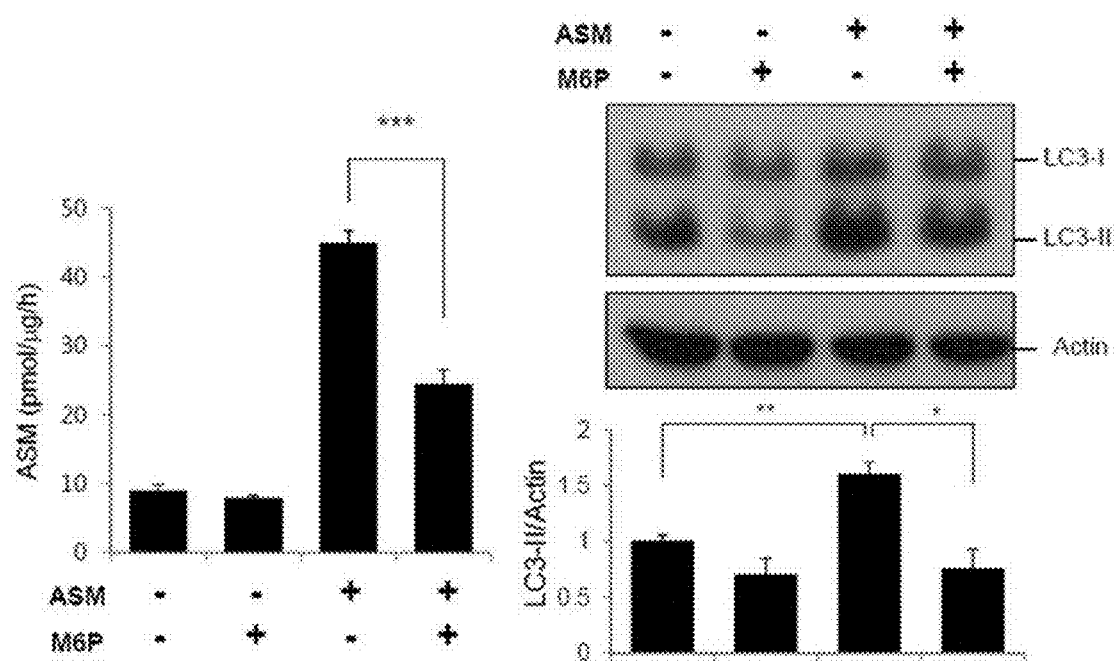
FIG. 19 is a view confirming the expression level of autophagy-related protein when treating human fibroblast with M6P using Western blotting and densitometric quantification.

As illustrated in FIG. 19, it is confirmed that when inhibiting the absorption of lysosome ASM using M6P, the conversion to LC3-II decreased, and accordingly the accumulation of ASM-induced autophagosome decreased.

In order to confirm whether ASM increases the formation rate of autophagosome, or decreases the degradation rate of autophagosome, autophagic flux assay was performed. More specifically, the conversion rate from LC3-I to LC3-II was measured in cells in the presence or absence of $NH_4Cl$, which inhibits degradation of autophagosome but does not affect autophagosome formation, using Western blotting. The results are illustrated in FIG. 20.

Figure 20:
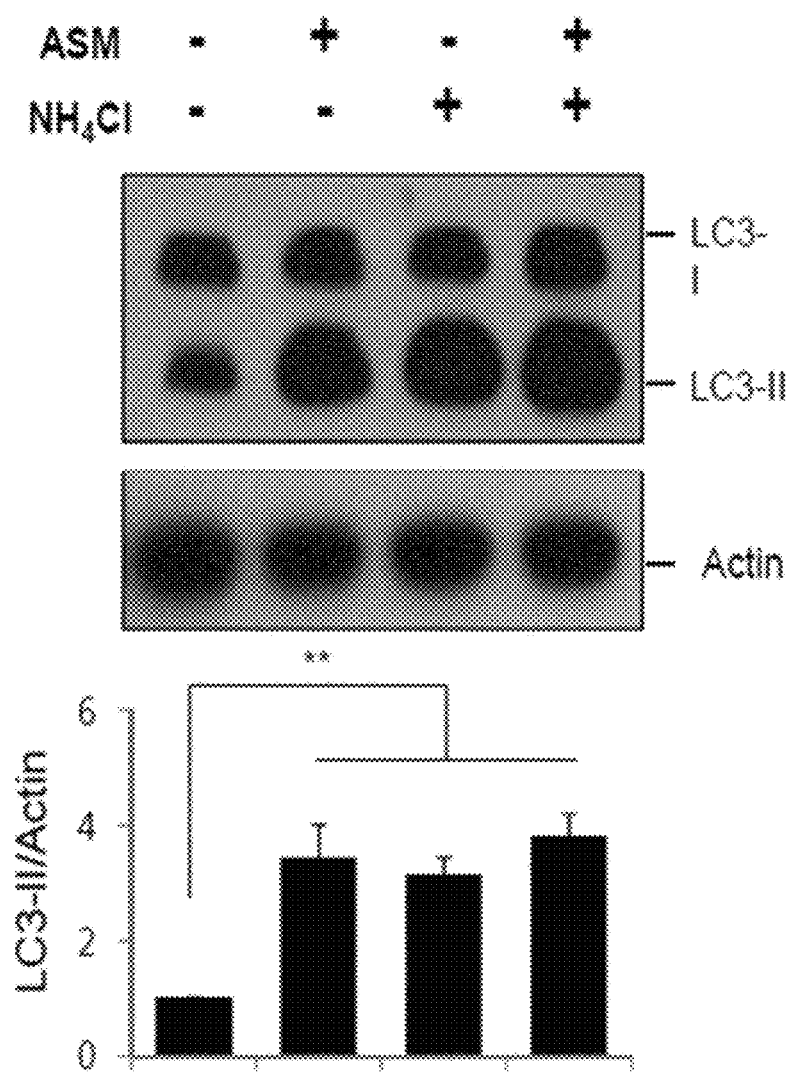
FIG. 20 is a view illustrating the conversion rate from LC3-I to LC3-II when treating human fibroblast with ASM in the presence or absence of NH$_4$Cl using Western blotting.

As illustrated in FIG. 20, it is confirmed that there is no significant change in the amount of LC3-II when treating cells with ASM and $NH_4Cl$.

Also, when treating with $NH_4Cl$ or ASM after culturing fibroblast of human with Alzheimer's disease in a serum-free medium or complete medium, the conversion rate from LC3-I to LC3-II was measured using Western blotting. The results are illustrated in FIG. 21 and FIG. 22.

Figure 21:
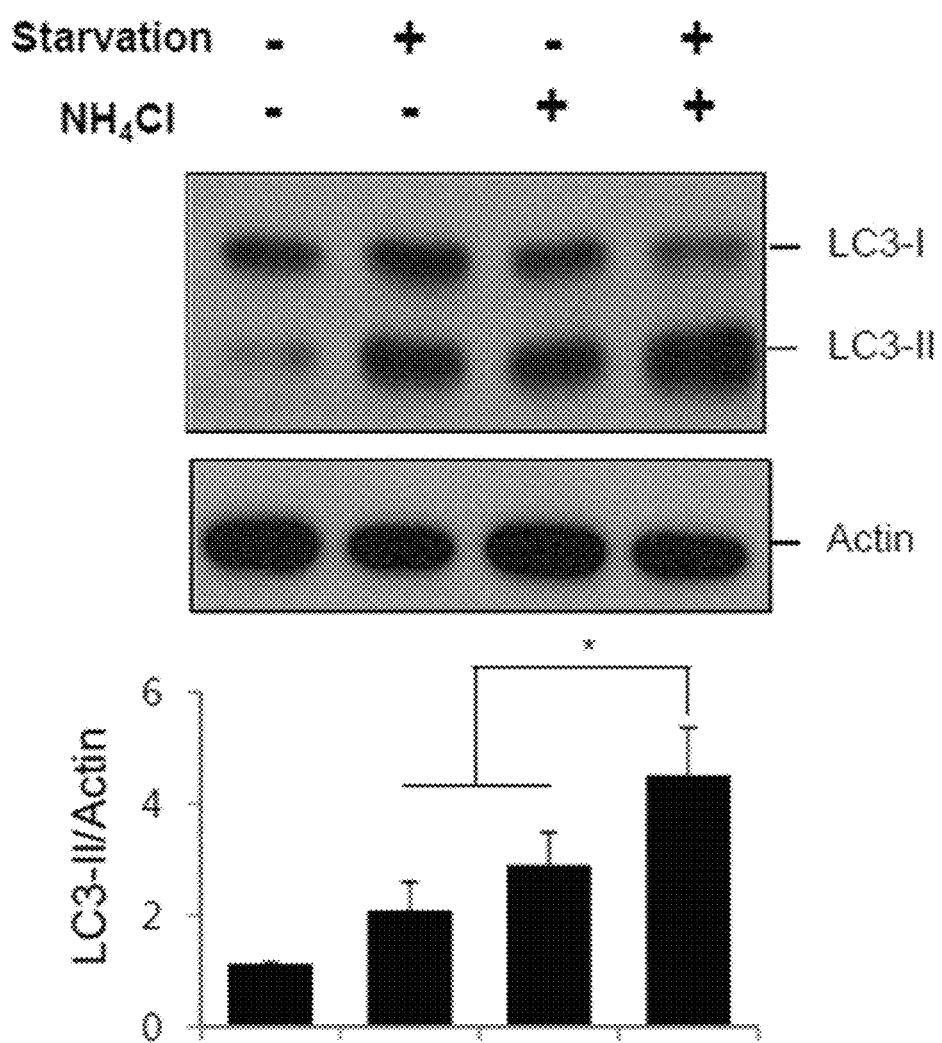
FIG. 21 is a view illustrating the conversion rate from LC3-I to LC3-II when culturing human fibroblast in a serum-free medium or complete medium and treating it with NH$_4$Cl.
Figure 22:
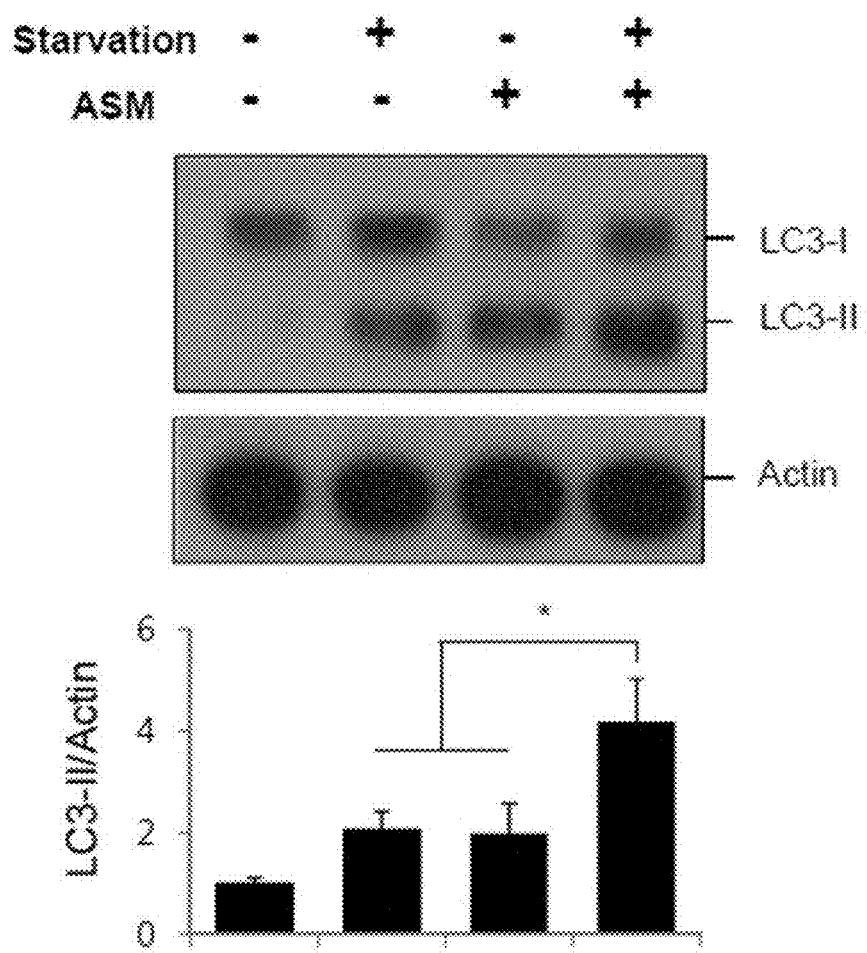
FIG. 22 is a view illustrating the conversion rate from LC3-I to LC3-II when culturing human fibroblast in a serum-free medium or complete medium and treating it with ASM.

As illustrated in FIG. 21, it is confirmed that the LC3-II level increased significantly when adding NH$_4$Cl after inducing autophagy by culturing cells in a serum-free medium. As illustrated in FIG. 22, it is confirmed that the accumulation of LC3-II increased significantly when treating with ASM after inducing autophagy by culturing cells in a serum-free medium.

Through the above test results, it is confirmed that ASM does not induce the formation of autophagosome in Alzheimer's disease, but inhibits proteolytic activity of autophagosome.

Figure 23:
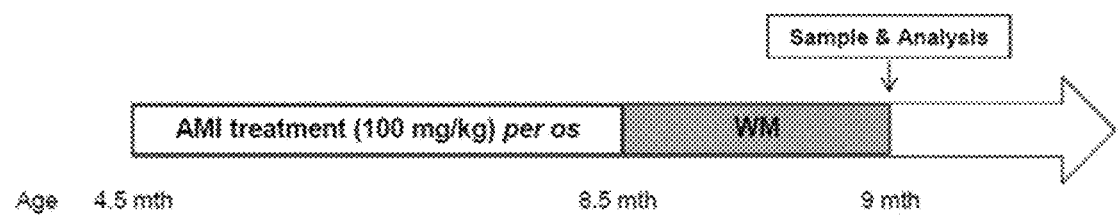
FIG. 23 is a view illustrating a test design for verifying the effect of treating Alzheimer's disease by administering AMI into APP/PS1 mice.
Figure 25:
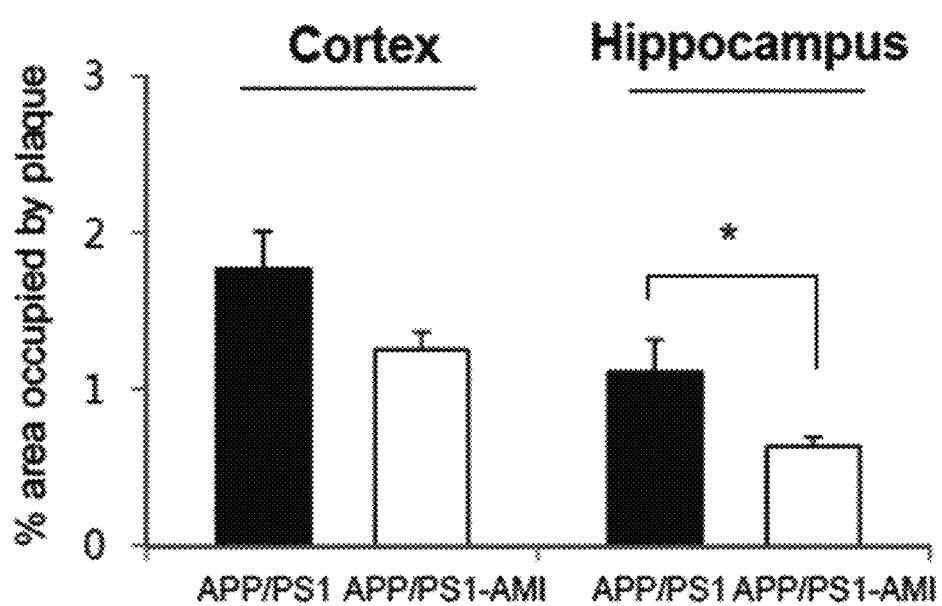
FIG. 25 is a view confirming the deposition of β-amyloid in the brain tissues (cerebral cortex and hippocampus) of mice when administering AMI into APP/PS1 mice.
Figure 26:
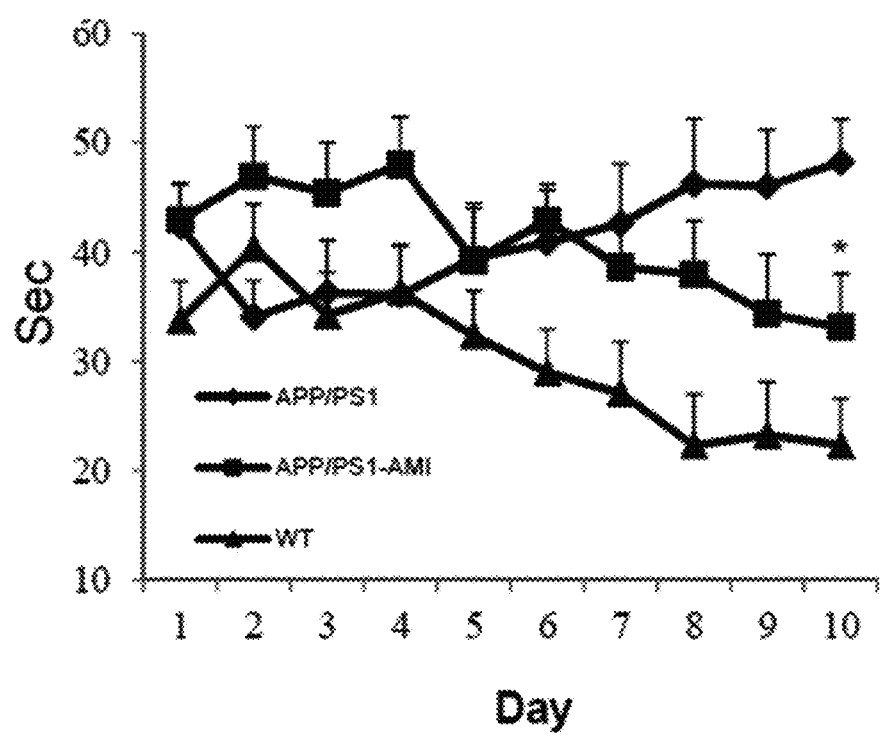
FIG. 26 is a view confirming the effect of improving the ability to remember when administering AMI into APP/PS1 mice and performing Morris water maze (MWM) test.

[Example 4] Verification on Pathological Improvement Effect of ASM Inhibition in Alzheimer Disease Model Mice 1. Verification on Effect of Treating Alzheimer's Disease after Administering AMI into APP/PS1 Mice AMI (amitriptyline-hydrochloride), which is a known inhibitor of ASM that can cross the blood-brain barrier (BBB), was administered to APP/PS1 mice, which are Alzheimer's disease model mice, for four months, and then the water maze (WM) test was performed (FIG. 23). The degree of ASM expression was measured by obtaining serum and brain tissue when the mice became nine month old (in the same manner as Example 1-2), and the deposition of β-amyloid in brain tissue was measured (in the same manner as Example 1-3). The test results are illustrated in FIGS. 24 to 26, respectively.

Figure 24:
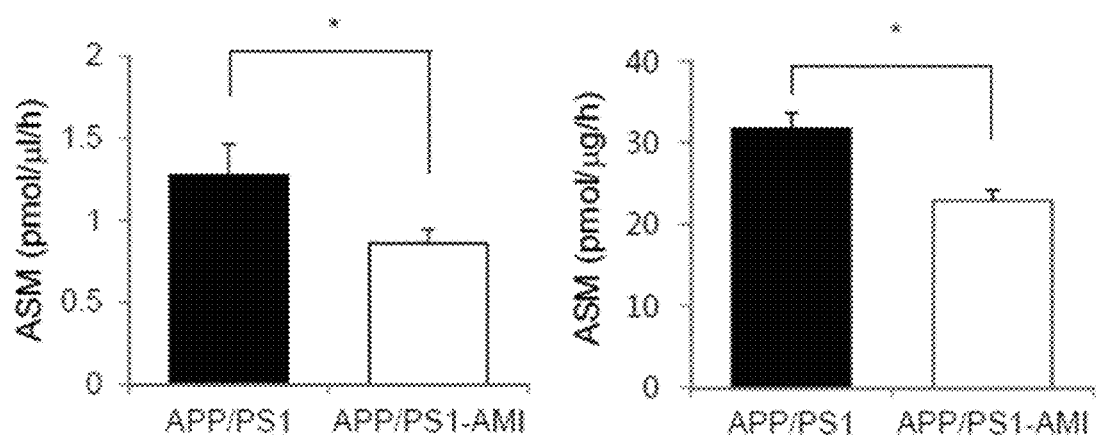
FIG. 24 is a view illustrating the ASM concentration in the serum and brain tissues of the mice when administering AMI into APP/PS1 mice.

As illustrated in FIG. 24, it is confirmed that ASM decreased in the serum and brain tissue of mice where AMI was administered. As illustrated in FIG. 25, it is confirmed that the deposition of β-amyloid was inhibited in the cerebral cortex and hippocampus of mice where AMI is administered. As illustrated in FIG. 26, it is confirmed that the ability to remember in mice where AMI is administered was recovered by decrease in escape latency, as compared to the control group.

Figure 27:
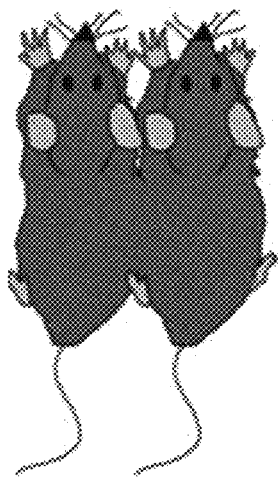
FIG. 27 is a view illustrating a test design for verifying the effect of treating Alzheimer's disease using parabionic union system [isochronic (APP/PS1-APP/PS1: parabionic union between APP/PS1 mice, which are Alzheimer's disease model mice), heterochronic I (APP/PS1-ASM$^{+/-}$: parabionic union between APP/PS1 mice and ASM$^{+/-}$ mice), heterochronic II (APP/PS1-WT: parabionic union between APP/PS1 mice and wild type mice)]
Figure 27:
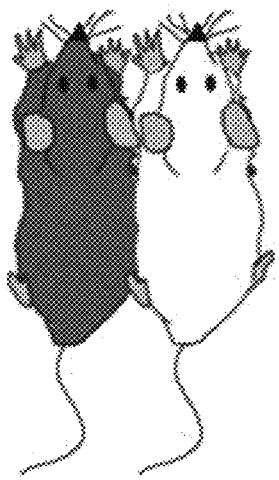
Figure 27:
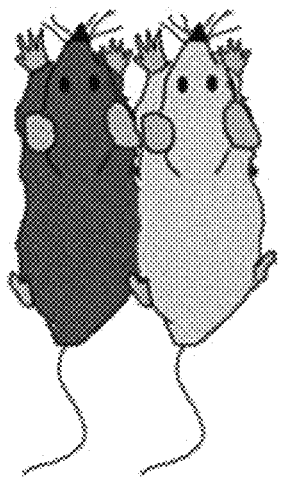

2. Verification on Effect of Treating Alzheimer's Disease Using Parabiotic System The effect of ASM inhibition is confirmed using parabiotic system of APP/PS1 mice. More specifically, isochronic (APP/PS1-APP/PS1: parabionic union between APP/PS1 mice, which are Alzheimer's disease model mice), heterochronic I (APP/PS1-ASM$^{+/-}$: parabionic union between APP/PS1 mice and ASM$^{+/-}$ mice), heterochronic II (APP/PS1-WT: parabionic union between APP/PS1 mice and wild mice) mice were prepared by sharing blood flow after connecting the skin and soft tissue by surgical methods and inducing new angiogenesis between two mice (FIG. 27). The expression degree of ASM was measured by obtaining serum and brain tissue in the same manner as Example 4-1, and the deposition of β-amyloid and expression of protein in brain tissue were measured. The test results are illustrated in FIGS. 28 to 30, respectively.

Figure 28:
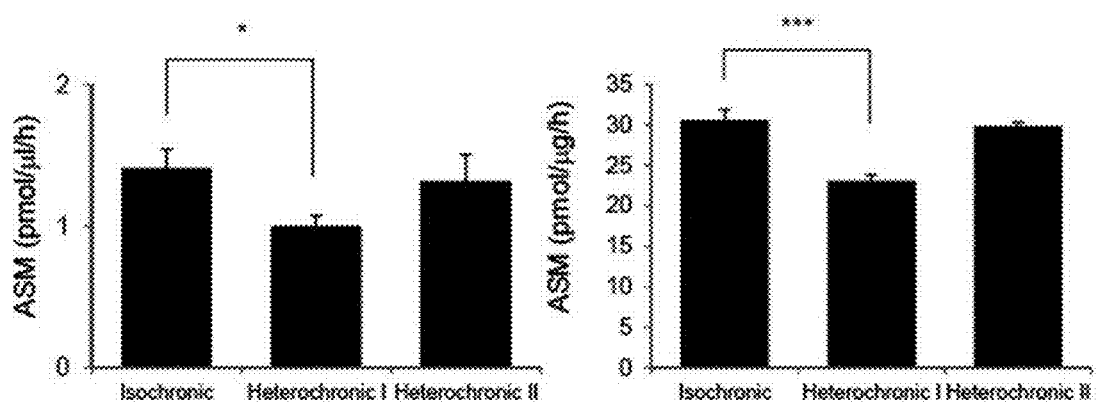
FIG. 28 is a view illustrating the ASM concentration in the serum and brain tissues of parabionic union mice.

As illustrated in FIG. 28, it is confirmed that the ASM concentration is low in the serum and brain tissue of heterochronic I (APP/PS1-ASM$^{+/-}$) mice, as compared to isochronic (APP/PS1-APP/PS1) and heterochronic II (APP/PS1-WT) mice, and thus ASM$^{+/-}$ mice play the role of lowering ASM concentration.

Figure 29:
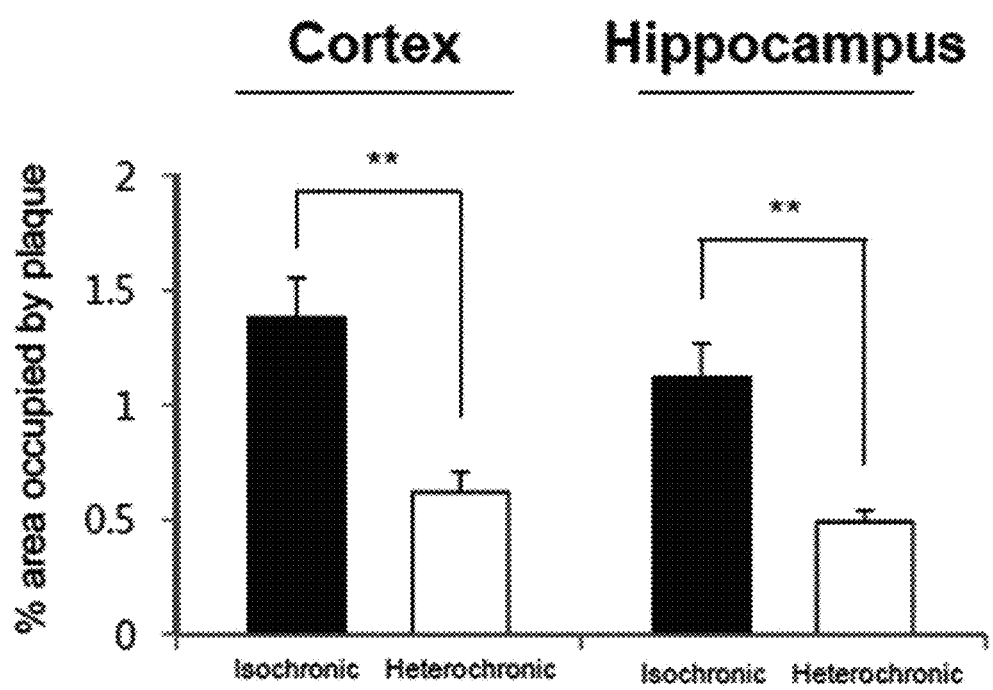
FIG. 29 is a view confirming the deposition of β-amyloid in the brain tissues (cerebral cortex and hippocampus) of parabionic union mice.

Also, as illustrated in FIG. 29, it is confirmed that the deposition of β-amyloid decreased remarkably in the cerebral cortex and hippocampus of heterochronic I (APP/PS1-ASM$^{+/-}$) mice, as compared to isochronic (APP/PS1-APP/PS1) mice.

Figure 30:
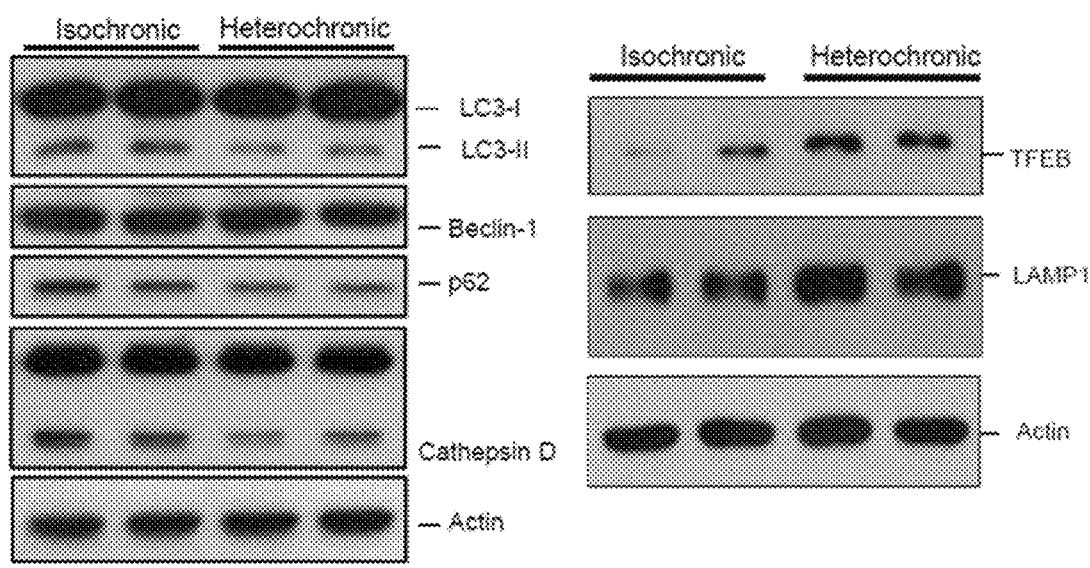
FIG. 30 is a view illustrating the expression level for each protein in the brain tissues of parabionic union mice using Western blotting.

Also, as illustrated in FIG. 30, it is confirmed that the conversion to LC3-II decreased, the expression of p62 and cathepsin D decreased, and the expression of TFEB and Lamp1, which are proteins relating to ALP function, increased in the brain tissue of heterochronic I (APP/PS1-ASM$^{+/-}$) mice, as compared to isochronic (APP/PS1-APP/PS1) mice.

3. Verification on Effect of Treating Alzheimer's Disease Using Serum Injection

Figure 31:
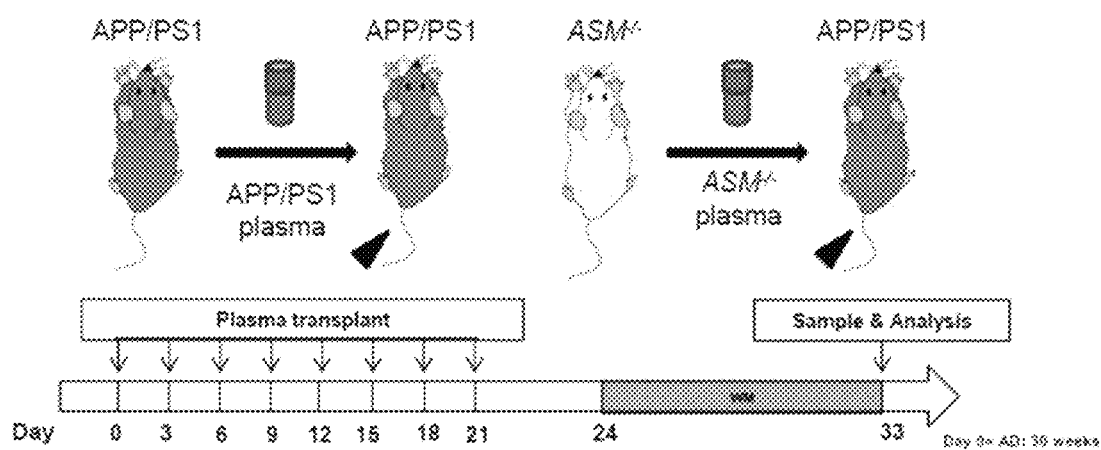
FIG. 31 is a view illustrating a test design for verifying the effect of treating Alzheimer's disease using serum injection.

The serum of APP/PS1 or ASM$^{-/-}$ mice was injected into APP/PS1 mice. More specifically, blood was obtained from the heart of APP/PS1 or ASM$^{-/-}$ mice, and then collected in a tube coated with EDTA. The collected blood was centrifuged to obtain serum, and 100 μl of serum was intravenously injected into an eight-month old APP/PS1 mice eight times during 3 weeks (FIG. 31). After the test was completed, the degree of ASM expression was measured by obtaining the serum and brain tissue in the same manner as in Example 4-1, and the deposition of β-amyloid and expression of protein in brain tissue were measured. Also, a behavior test was performed in the same manner as Example 1-4. The test results are illustrated in FIGS. 32 to 36.

Figure 32:
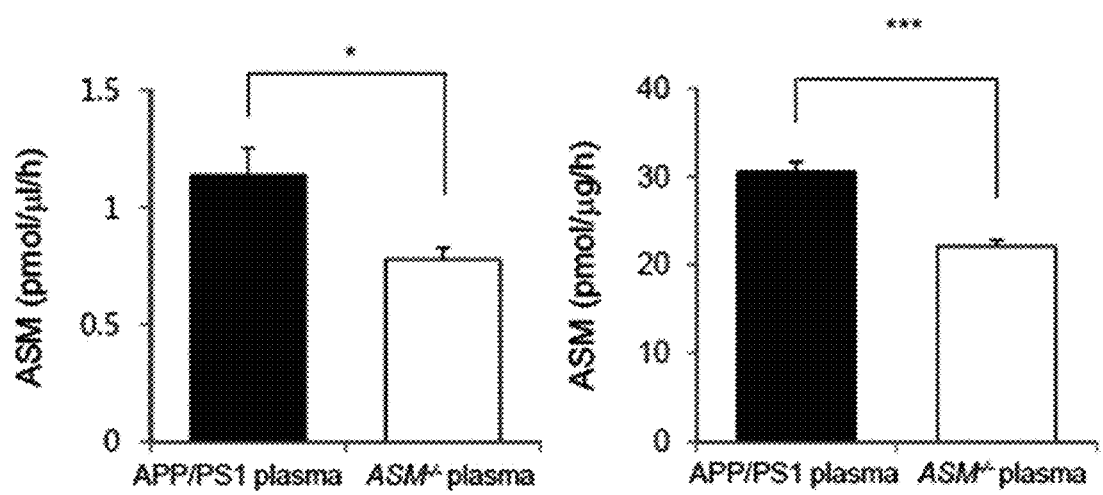
FIG. 32 is a view illustrating the ASM concentration in serum and brain tissues of APP/PS1 mice provided with serum of each mouse.

As illustrated in FIG. 32, it is confirmed that the ASM decreased in the serum and brain tissue of APP/PS1 mice provided with serum of ASM$^{-/-}$ mice, as compared to the APP/PS1 mice provided with serum of APP/PS1 mice.

Figure 33:
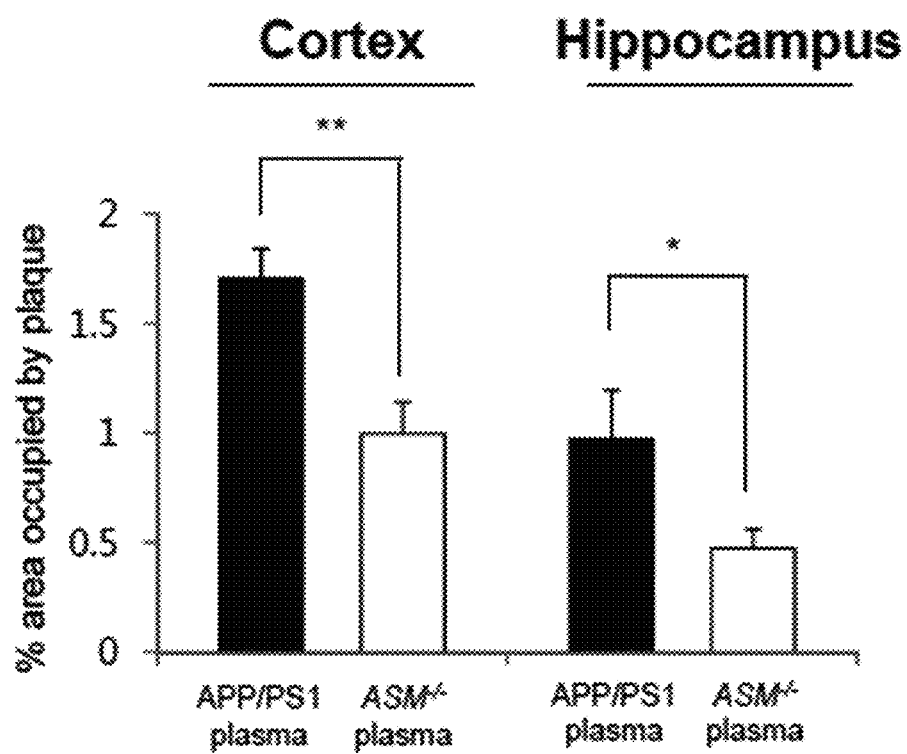
FIG. 33 is a view confirming the deposition of β-amyloid in the brain tissues (cerebral cortex and hippocampus) of APP/PS1 mice provided with serum of each mouse.
Figure 34:
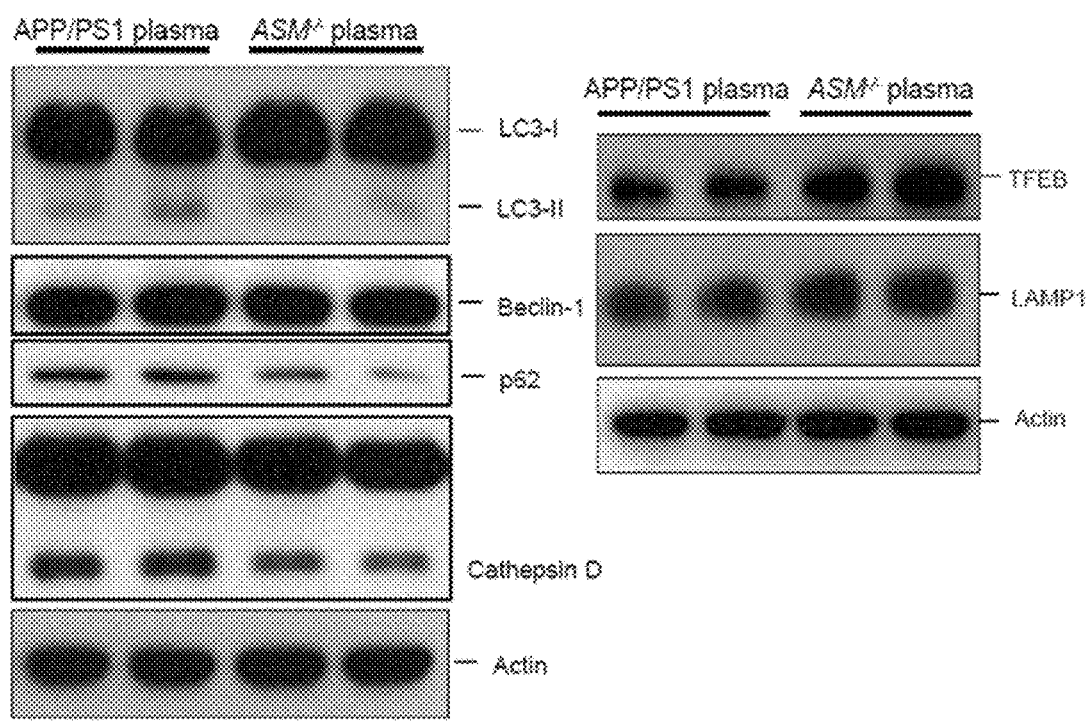
FIG. 34 is a view illustrating the expression level for each protein in the brain tissue of APP/PS1 mice provided with serum of each mouse using Western blotting.

As illustrated in FIG. 33 and FIG. 34, it is confirmed that the deposition of β-amyloid decreased (FIG. 33), the conversion to LC3-II decreased, and the expression of p62 and cathepsin D decreased (FIG. 34) in the brain tissue of APP/PS1 mice provided with serum of ASM$^{-/-}$ mice, as compared to the APP/PS1 mice provided with serum of APP/PS1 mice.

Figure 35:
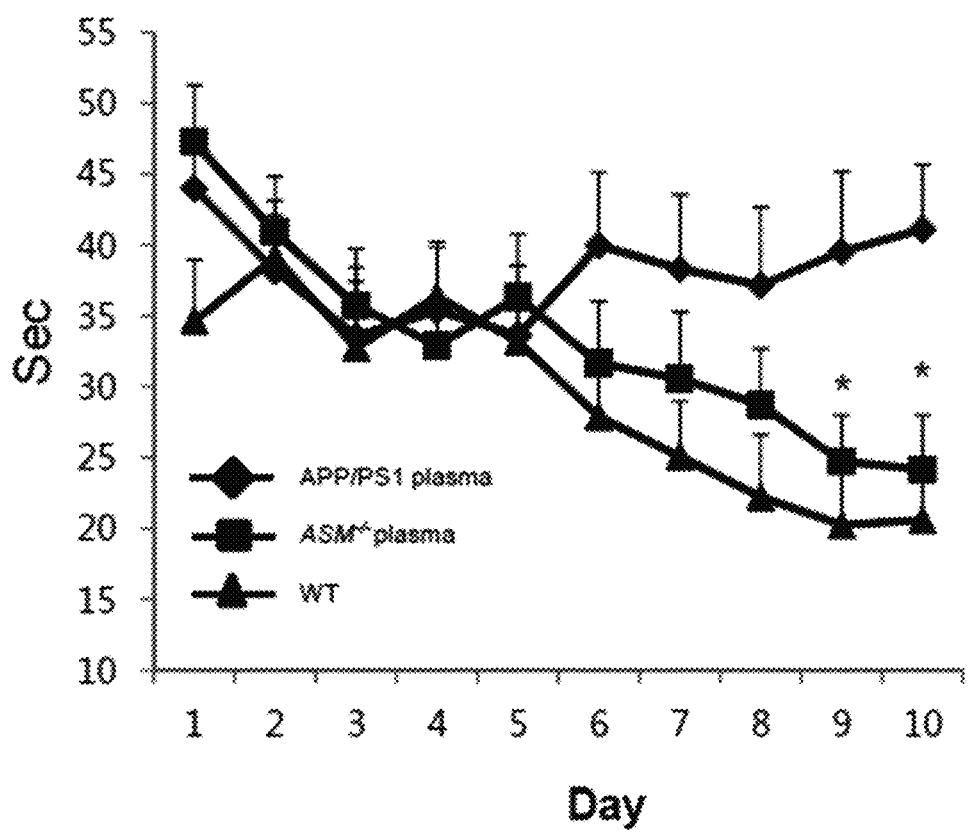
FIG. 35 is a view confirming the effect of improving the ability to remember of APP/PS1 mice provided with serum of each mouse using Morris water maze (MWM) test.
Figure 36:
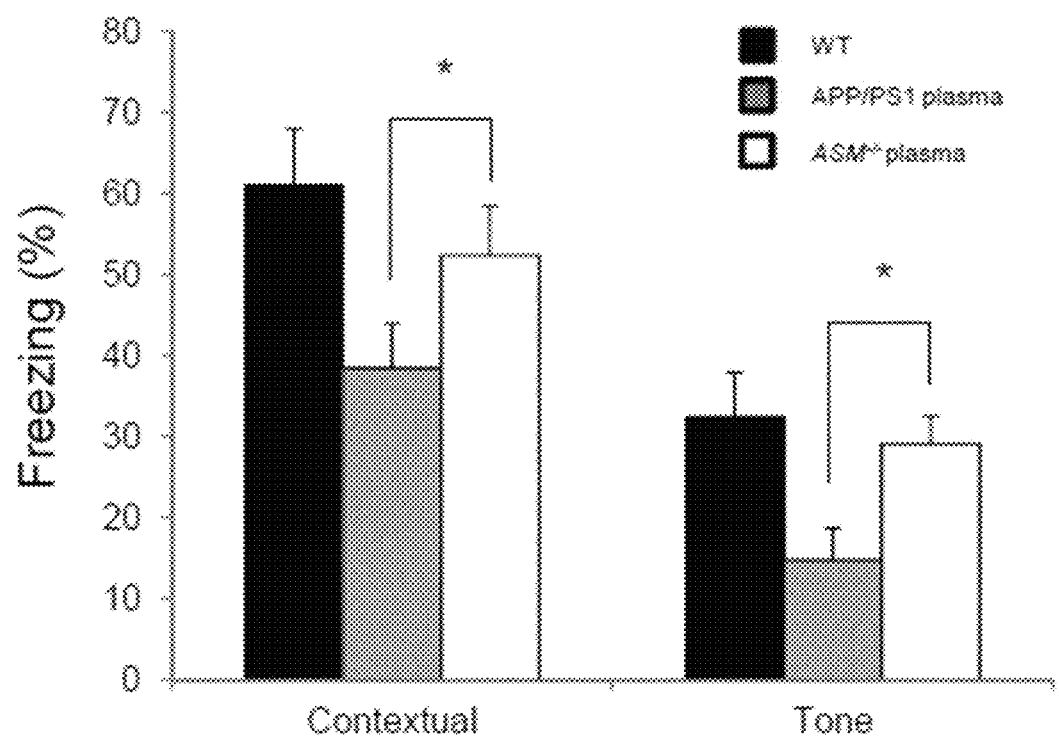
FIG. 36 is a view confirming the effect of improving the ability to remember of APP/PS1 mice provided with serum of each mouse using fear conditioning test.
Figure 37:
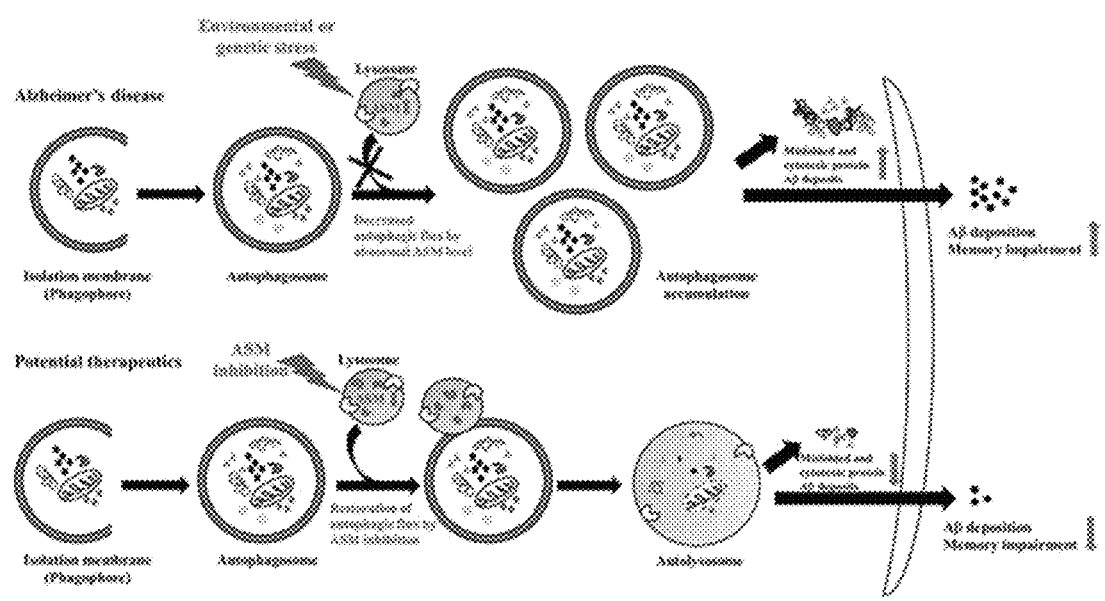
FIG. 37 is a schematic diagram of the role of ASM to a pathogenesis of Alzheimer's disease.

As illustrated in FIG. 35 and FIG. 36, as a result of MWM and fear conditioning test, it is confirmed that the ability to remember improved in APP/PS1 mice provided with serum of ASM$^{-/-}$ mice, as compared to APP/PS1 mice provided with serum of APP/PS1 mice.

Hereinafter, preparation examples of the pharmaceutical composition and food composition of the present invention are described for illustrative purposes only, and the present invention is not intended to be limited by the following preparation examples.

Preparation Example 1. Preparation of a Pharmaceutical Formulation 1-1. Preparation of Powders
ASM expression inhibitor or activity inhibitor 2 g lactose 1 g
The above ingredients were mixed and filled into a sealed pouch to prepare a powder formulation.

1-2. Preparation of a Tablet
ASM expression inhibitor or activity inhibitor 100 mg
corn starch 100 mg
lactose 100 mg
stearic acid magnesium 2 mg
The above ingredients were mixed, and then tabulated according to a conventional tablet preparation method to prepare a table formulation.

1-3. Preparation of a Capsule
ASM expression inhibitor or activity inhibitor 100 mg
corn starch 100 mg
lactose 100 mg
stearic acid magnesium 2 mg The above ingredients were mixed, and then filled into a gelatin capsule according to a conventional capsule preparation method to provide a capsule formulation.

Preparation Example 2. Preparation of Food Formulation 2-1. Preparation of Health Care Food

| | |
|---|---:|
| ASM expression inhibitor or activity inhibitor | 100 mg |
| vitamin mixture | proper quantity |
| vitamin A acetate | 70 g |
| vitamin E | 1.0 mg |
| vitamin B1 | 0.13 mg |
| vitamin B2 | 0.15 mg |
| vitamin B6 | 0.5 mg |
| vitamin B12 | 0.2 g |
| vitamin C | 10 mg |
| biotin | 10 g |
| nicotinic acid amid | 1.7 mg |
| folic acid | 50 g |
| calcium pantothenate | 0.5 mg |
| inorganic mixture | proper quantity |
| ferrous sulfate | 1.75 mg |
| zinc oxide | 0.82 mg |
| magnesium carbonate | 25.3 mg |
| potassium phosphate monobasic | 15 mg |
| calcium phosphate dibasic | 55 mg |
| potassium citrate | 90 mg |
| calcium carbonate | 100 mg |
| magnesium chloride | 24.8 mg |

In the above composition ratio including vitamins and minerals, the ingredients are mixed in a ratio appropriate for a health care food, but the mixing ratio may be changed. A health care food composition may be prepared according to a conventional method of preparing a health care food, the method including the steps of mixing the above ingredients, preparing granules, and using the granules in the same manner as the conventional method.

The invention claimed is:

1. A method for screening a substance for potentially treating Alzheimer's disease, the method comprising:
    a) applying a candidate substance to a transformed host cell expressing acid sphingomyelinase (ASM) protein;
    b) performing an assay to obtain an expression amount of ASM protein expressed in the transformed host cell in step (a);
    c) comparing the expression amount of ASM-protein in step (b) to an expression amount of ASM-protein in a control transformed host cell expressing ASM-protein where the candidate substance is not applied thereto, wherein a decrease in the expression amount of ASM-protein in the transformed host cell in comparison to the control transformed host cell is indicative of a candidate substance for potentially treating Alzheimer's disease.

2. The method according to claim 1, wherein step (b) or (c) is conducted using at least one method selected from a group consisting of Western blotting, enzyme linked immunosorbent assay (ELISA), radioimmunoassay (RIA), radioimmunodiffusion, Ouchterlony immunodiffusion, rocket immunoelectrophoresis, immunohistostaining, immunoprecipitation assay, complement fixation assay, fluorescence activated cell sorter (FACS) and protein chip.

3. The method of claim 1, wherein the transformed host cell is an isolated transformed eukaryotic animal cell.

* * * * *